United States Patent
Ackerman et al.

(10) Patent No.: US 6,185,444 B1
(45) Date of Patent: Feb. 6, 2001

(54) SOLID-STATE MAGNETIC RESONANCE IMAGING

(75) Inventors: Jerome L. Ackerman, Newton; Melvin J. Glimcher, Boston; Yaotang Wu, Watertown, all of MA (US)

(73) Assignee: SkelScan, Inc., Newton, MA (US)

( * ) Notice: Under 35 U.S.C. 154(b), the term of this patent shall be extended for 0 days.

(21) Appl. No.: 09/041,981

(22) Filed: Mar. 13, 1998

(51) Int. Cl.$^7$ .................................................. A01B 5/055
(52) U.S. Cl. .......................... 600/410; 600/420; 324/309
(58) Field of Search .................................. 324/307, 309, 324/306; 600/410, 420

(56) References Cited

U.S. PATENT DOCUMENTS

| | | | |
|---|---|---|---|
| 4,431,968 | * 2/1984 | Edelstein et al. | 324/309 |
| 4,510,450 | 4/1985 | Brown | 324/321 |
| 4,635,643 | 1/1987 | Brown | 128/653 |
| 4,775,522 | * 10/1988 | Clark, Jr. | 600/410 |
| 4,871,967 | * 10/1989 | Rotem et al. | 324/309 |
| 4,902,973 | * 2/1990 | Keren | 324/312 |
| 4,922,915 | 5/1990 | Arnold et al. | 128/653 |
| 4,939,464 | * 7/1990 | Hammer | 324/318 |
| 5,247,934 | 9/1993 | Wehrli et al. | 128/653 |
| 5,270,651 | 12/1993 | Wehrli | 324/308 |
| 5,322,065 | * 6/1994 | Leunbach | 600/420 |
| 5,789,021 | 8/1998 | Albert et al. | 324/300 |
| 6,010,681 | * 1/2000 | Margerum et al. | 424/9.35 |

OTHER PUBLICATIONS

Charles W. Stearns et al., "Three Dimensional Image Reconstruction in the Fourier Domain", IEEE Transactions on Nuclear Science, vol. NS–34, vol. 1, Feb. 1987, pp. 374–378.

D.A. Chester et al., "Rapid 3–D Reconstruction from 1–D Projections for Metabolic MR Imaging of Short T, Species", 1992 SMRM, Berlin, p. 665.

Charles Eric Brown et al., "In Vivo $^{31}$P Nuclear Magnetic Resonance Spectroscopy of Bone Mineral for Evaluation of Osteoporosis", Clin. Chem. 34/7, 1431–1438 (1988).

Joseph H. Battocletti et al., "Design of a Low–Field NMR Spectrometer to Measure Bone Mineral", Journal of Clinical Engineering, vol. 15, No. 6, Nov.–Dec., pp. 479–487, 1990.

C.W. Stearns et al., "Accelerated Image Reconstruction for a Cylindrical Positron Tomograph Using Fourier Domain Methods", IEEE Transportation on Nuclear Science, vol. 37, No. 2, pp. 773–777, Apr. 1990.

Yaotang Wu et al., "A Unique Protonated Phosphate Group in Bone Mineral Note Present in Synthetic Calcuim Phosphates, Identification by Phosphorous–31 Solid State NMR Spectroscopy", J.Mol.Biol. (1994) 244, 423–435.

Jerome L. Ackerman et al., "Fluid and Solid State MRI of Biological and Nonbiological Ceramics", Magnetic Resonance Microscopy, Methods and Application in Material Science, Agriculture and Biomediine, 1992.

Jerome L. Ackerman, Ph.D., "MR Imaging and Spectroscopy of Phosphorus in Bone Mineral", NIH grant application Oct. 30, 1991.

Rasesh D. Kapadia et al., "Magnetic Resonance Microscopy in Rat Skeletal Research", MRM 30:247–250 (1993).

Charles Eric Brown et al., "Comparison of the Compression Strength of Human Vertebral Bodies with the Mass and Density of Apatite: a Study by $^{31}$P NMR Spectroscopy", Clincal Chemistry, 34/10, 2114–2117 (1988).

(List continued on next page.)

*Primary Examiner*—Brian L. Casler
(74) *Attorney, Agent, or Firm*—Fish & Richardson P.C.

(57) ABSTRACT

Principles of magnetic resonance are employed to generate data, such as image intensity data, reflecting the spatial distribution of one or more isotopes carried in a solid-state specimen such as bone. The spatial distribution data can be employed, e.g., to calculate bone mineral density and/or degree of mineralization.

75 Claims, 8 Drawing Sheets

OTHER PUBLICATIONS

Chandrasekhar Ramanathan et al., "ADRF–CP Surface–Coil Spectroscopy of Synthetic Calcium Phosphates and Bone Mineral", Journal of Magnetic Resonance, Series A 121, 127–138 (1996), Article No. 0152.

Chandrasekhar Ramanathan et al."ADRF Differential Cross Polarization Spectroscopy of Synthetic Calcuim Phosphates and Bone Mineral", Journal of Magnetic Resonance, 127, 26–35 (1997), Article No. MN971173.

A. Pines et al., "Proton–enhanced NMR of dilute spins in solids", The Journal of Chemical Physics, vol. 59, No. 2, Jul. 15, 1973, pp. 569–590.

James R. Moore et al., "Solid State Phosphorus–31 Magnetic Resonance Imaging of Bone Mineral", Magnetic Resonance in Medicine, pp. 293–299, 1995.

John Pauly et al., "Slice–Selective Excitation for Very Short $T_2$ Species", Eighth Annual Meeting, Society of Magnetic Resonance in Medicine, Amsterdam, Aug. 12–18, 1989.

George W. Kabalka et al., "Boron–11 MRI and MRS of Intact Animals Infused with a Boron Neutron Capture Agent", Magnetic Resonance in Medicine 8, 231–237 (1988).

Peter Bendel et al., "A Method for Imaging Nuclei with Short $T_2$ Relaxation and Its Application to Boron–11 NMR Imaging of a BNCT Agent in an Intact Rat", Journal of Magnetic Resonance 88, 369–375 (1990).

Pratik Ghosh et al., "Pure Phase–Encoded MRI and Classification of Solids", IEEE Transactions on Medical Imaging, vol. 14, No. 3, Sep. 1995, pp. 616–620.

Charles Eric Brown et al., "Noninvasive Evaluation of Mineral Content of Bone without Use of Ionizing Radiation", Clin. Chem. 33/2, 227–236 (1987).

X. Marchandise et al., "Solid State Phosphorus NMR Spectroscopy Quantitative Evaluation of Biomaterials for Applications as Bone Substitutes", SMRM 1988.

John C. Ford et al., "In Vivo Quantitative Characterization of Trabecular Bone by NMR Interferometry and Localized Proton Spectroscopy", Magnetic Resonance in Medicine 17, 543–551 (1991).

J.P. Mattei et al., "Variations of In Vivo Pseudo–T1 Relaxation Time in Phosphorus–31 MRS of Bone Failes to Diagnose Osteoporosis", SMRM, p. 1121.

Michael Dolecki et al., "A Phosphorus NMR Spectroscopy Technique for Measuring Bone Density In vitro and In vivo Studies", SMRM 1990, p. 1229.

S. Confort–Gouny et al., "Phosphorus–31 In Vivo Magnetic Resonance Spectroscopy of Bone Fails to Diagnose Osteoporosis", Calcif Tissue Int. (1995) 56:529–532.

Limin Li et al., "Phosphorus–31 Magnetic Resonance Imaging in Ex–Vivo Beef Bone", SMRM 1988, p. 51.

Jerome L. Ackerman et al., "Solid State NMR in Living Subjects", Second International Conference on NMR Microscopy, Heidelberg, Germany, Sep. 6–10, 1993.

David P. Madio et al., "Ultra–Fast Imaging Using Low Flip Angles and FIDs", MRM 34:525–529 (1995).

Xiahong Zhou et al., "NMR Microscopy Using Projection Reconstruction", Magnetic Resonance Microscopy, Methods and Application in Materials Science, Agriculture and Biomedicine, 1992.

T.J. Myers et al., "Comparison of Nuclear Magnetic Resonance Spectroscopy with Dual–Photon Absorptiometry and Dual–Energy X–Ray Absorptiometry in the Measurement of Thoracic Vertebral Bone Mineral Density: Compressive Force Versus Bone Mineral", Osteoporosis Int. (1994) 4:129–137.

PCT Search Report.

S.L. Dieckman et al., "Three Dimensional Nuclear Magnetic Resonance and X–Ray Microtomographic Imaging of Composite Materials", Mat. Res. Soc. Proc. (1991), vol. 217, pp. 169–180.

Callaghan, NMR Imaging in the Solid State, Principles of Nuclear Magnetic Resonance Microscopy, (1981) pp. 306–327.

Komoroski et al., "NMR Imaging of Elastomers and Porous Media", Mat. Res. Soc. Proc. held Nov. 28, 1990, vol. 217, pp. 3–14.

Cory et al., "NMR Imaging of Solids Using Imaging Instrumentation Designed for Liquids", Mat. Res. Soc. Symp. Proc. held Nov. 28, 1990, vol. 217, pp. 15–20.

Kordas et al., "Three Dimensional (3D) Electron Paramagnetic Resonance Imaging Technique for Mapping Porosity in Ceramics", Mat. Res. Soc. Symp. Proc. held Nov. 28, 1990, vol. 217, pp. 21–25.

Pfleiderer et al., "Imaging of Diffusion Processes in Differently Crosslinked Polystyrenes by $^1H$ and $^{19}F$–Microscopy", Mat. Res. Soc. Symp. Proc. held Nov. 28, 1990, vol. 217, pp. 27–32.

Kuhn et al., "Characterization of Stressed and Crosslinked Polymers by $^{13}C$–CP/MAS and NMR Imaging", Mat. Res. Soc. Symp. Proc. held Nov. 28, 1990, vol. 217, pp. 33–42.

Majors et al., "Fast Radial NMR Imaging of Transport Processes", Mat. Res. Soc. Symp. Proc. held Nov. 28, 1990, vol. 217, pp. 43–47.

Garrido et al., "Characterization of Biomaterials with NMR", Mat. Res. Soc. Symp. Proc. held Nov. 28, 1990, vol. 217, pp. 49–54.

Schuff et al., "A Study of Change in Poly(Methyl Methacrylate) (pMMA) Resulting from the Adsorption of Methanol Using NMR Imaging", Mat. Res. Soc. Symp. Proc. held Nov. 28, 1990, vol. 217, pp. 55–60.

Mateescu et al., "Oxygen–17 and Proton MR Microscopy in Materials Analysis", Mat. Res. Soc. Symp. Proc. held Nov. 28, 1990, vol. 217, pp. 61–66.

Suits, "NMR Imaging and the Electric Quadrupole Interaction in Solid Materials", Mat. Res. Soc. Symp. Proc. held Nov. 28, 1990, vol. 217, pp. 67–72.

Sinton et al., "NMR Imaging of Industrial Flow Processes", Mat. Res. Soc. Symp. Proc. held Nov. 28, 1990, vol. 217, pp. 73–78.

Mehring, Principles of High Resolution NMR In Solids, (1976), pp. 63–185.

Glimcher, "Chapter 2: The Nature of the Mineral Phase in Bone: Biological and Clinical Implications", Metabolic Bone Disease, (1997), pp. 23–50.

Termine et al., "Infrared Analysis of Rat Bone: Age Dependence of Amorphous and Crystalline Mineral Fractions", Science, 153, Sep. 1966, pp. 1523–1525.

Nancollas et al., "Mineral Phases of Calcium Phosphate", The Anatomical Record 224:234–241 (1989).

Wuthier et al., "Mechanism of Matrix Vesicle Calcification: Characterization of Ion Channels and the Nucleational Core of Growth Plate Vesicles", Bone and Mineral, 17 (1992) 290–295.

Rey et al., "Maturation of Poorly Crystalline Apatites: Chemical and Structural Aspects In Vivo and In Vitro", Cells and Materials, vol. 5, No. 4, 1995 (pp. 345–356).

Cory, "Solid State NMR Imaging", Annual Reports on NMR Spectroscopy, (1992) vol. 24, pp. 88–180.

Ebifegha et al., "In Vivo Analysis of Bone Fluoride Content Via NMR", Phys. Med. Biol., 1987, vol. 32, No. 4, pp. 439–451.

Ackermann et al., "Fluid and Solid State MRI of Biological and Non Biological Ceramics", Magnetic Resonance Microscopy. Methods and Applications in Materials Science, Agriculture and Biomedicine, (1992) pp. 237–260.

Meunier et al., "Bone Mineral Density Reflects Bone Mass but Also the Degree of Mineralization of Bone: Therapeutic Implications", Bone, vol. 21, No. 5, Nov. 1994:373–377.

Moore et al., "Magnetic Resonance Imaging of Specific Chemical Constituents in Ceramic Powders and Dense Bodies", Ceram. Engl. Sci. Proc. 11[9–10], (1990), pp. 1302–1319.

Suits et al., "NMR Imaging In Solids", Solid State Communications, vol. 50, No. 4, (1984), pp. 291–295, 1984.

Sherman et al., "NIA Workshop on Aging and Bone Quality", Calcif Tissue Int. (1993) 53 (Suppl. 1).

Miller et al., "Consensus of an International Panel on the Clinical Utility of Bone Mass Measurements in the Detection of Low Bone Mass in the Adult Population", Calcif Tissue Int. (1996) 58: 207–214.

Lenchik et al., "Current Concepts in Osteoporosis", AJR: 168, Apr. 1997, pp. 905–911.

Jara et al., "High Resolution Variable Flip Angle 3D MR Imaging of Trabecular Microstructure in Vivo", MRM 29:528–239 (1993) 7.

Ouyang et al., "High Resolution Magnetic Resonance Imaging of the Calcaneus: Age–Related Changes in Trabecular Structure and Comparison with Dual X–Ray Absorptiometry Measurements", Calcif Tissue Int. (1997) 60:139–147.

Majumdar et al., "Quantitation of the Susceptibility Difference between Trabecular Bone and Bone Marrow: Experimental Studies", Magnetic Resonance in Medicine 22, 111–127 (1991).

Ford et al., "Magnetic Field Distribution in Models of Trabecular Bone", MRM 30:373–379 (1993).

Kohler et al., "NMR Chemical Shielding Tensors of $-Ca_2P_2O_7$", The Journal of Chemical Physics, vol. 64, No. 11, Jun. 1, 1976, pp. 4451–4458.

Rothwell et al., "High Resolution Variable–Temperature $^{31}P$ NMR of Solid Calcium Phosphates", Journal of the American Chemical Society, 102:8, Apr. 9, 1980, pp. 2637–2643.

Herzfeld et al., "Magic Angle Sample Spinning in Inhomogeneously Broadened Biological Systems", Phil. Trans. R. Soc. Lond. B 289, 459–469 (1980).

Glimcher et al., "Recent Studies on Bone Mineral: Is the Amorphous Calcium Phosphate Theory Valid?", Journal of Crystal Growth 53 (1981) 100–119.

Aue et al., "Solid State Phosphorus–31 Nuclear Magnetic Resonance Studies on Synthetic Solid Phases of Calcium Phosphate: Potential Models of Bone Mineral", Biochemistry, vol. 23, No. 25, 1984, pp. 6110–6114.

Roufosse et al., "Investigation of the Mineral Phases of Bone by Solid–State Phosphorus–31 Magic Angle Sample Spinning Nuclear Magnetic Resonance", Biochemistry, vol. 23, No. 25, 1984, pp. 6115–6120.

Harris et al., "Line Narrowing in Phosphorus–31 Spectra of Solids Using a Combination of High–Power Decoupling, Cross–Polarization, Magic–Angle Spinning, and $^{31}P$ Multiple–Pulse Operation", Journal of Magnetic Resonance 73, 178–183 (1987).

Yesinowski et al., "Hydrogen Environments in Calcium Phosphates: $^1H$ MAS NMR at High Spinning Speeds", J. Am. Chem. Soc., vol. 109, No. 21, 1987, pp. 6274–6282.

Dawson et al., "Solid–State Phosphorus–31 Nuclear Magnetic Resonance Differentiation of Bone Mineral and Synthetic Apatite Used to FH1 Bone Defects", Investigative Radiology, Nov. 1991, vol. 26, No. 11, pp. 946–950.

Rey et al., "Structural Studies of the Mineral Phase of Calcifying Cartilage", Journal of Bone and Mineral Research, vol. 6, No. 5, 1991, pp. 515–525.

Roberts et al., "Characterization of Very Young Mineral Phases of Bone by Solid State $^{31}$Phosphorus Magic Angle Sample Spinning Nuclear Magnetic Resonance and X–Ray Diffraction", Calcif Tissue Int. (1992) 50:42–48.

Roberts et al., "Solid State $^{31}$NMR Studies of the Convesion of Amorphous Tricalcium Phosphate to Apatitic Tricalcium Phosphate", Calcif Tissue Int. (1991) 49:378–382.

Bonar et al., "Structural and Composition Studies on the Mineral of Newly Formed Dental Enamel: A Chemical, X–ray Diffraction, and $^{31}P$ and Proton Nuclear Magnetic Resonance Study", Journal of Bone and Mineral Research, vol. 6, No. 11, 1991, pp. 1167–1176.

Marchandise et al., "Solid–State $^{31}P$ NMR Spectroscopy of Bone and Bone Substitutes", Magnetic Resonance in Medicine 28, 1–8 (1992).

Santos et al., "Communications $^1H$ Cramps and $^1H–^{31}P$ HetCor Experiments on Bone, Bone Mineral, and Model Calcium Phosphate Phases", Journal of Magnetic Resonance, Series B 105, 183–187 (1994).

Code et al., "In Vivo $^{19}F$ Spin Relaxtion in Indx Finger Bones", Magnetic Resonance in Medicine 13, 358–369 (1990).

Ebifegha et al., "In vivo analysis of bone with solid echoes combined with refocused gradients", Phys. Med. Biol., 1990, vol. 35, No. 8, 1153–1158.

Li et al., "$^{31}P$ NMR imaging of solid bone with solid echoes combined with refocused gradients", Phys. Med. Biol., 1990, vol. 35, No. 8, 1153–1158.

Ackermann et al., "Phosphorus–31 Magnetic Resonance Imaging of Hydroxyapatite: A Model for Bone Imaging", Magnetic Resonance in Medicine 25, 1–11 (1992).

Bartlett, "Phosphorus Assay in Column Chromatography", (1959), vol. 234, No. 3, pp. 466–468.

Fiske et al., "The Colorimetric Determination of Phosphorus", The Journal of Biological Chemistry, vol. LXVI, No. 2, (1925), pp. 375–400.

Hangartner et al., "Influence of fat on bone measurements with dual–energy absorptiometry", Bone and Mineral, 9 (1990) 71–81.

Mitlak et al., "Accuracy, Precision, and Utility of Spine and Whole–Skeleton Mineral Measurements of DXA in Rats", Journal of Bone and Mineral Research, vol. 9, No. 1, 1994, pp. 119–126.

Sabin et al., "The Accuracy of Volumetric Bone Density Measurements in Dual X–Ray Absorptiometry", Calcif Tissue Int. (1995) 56:210–214.

Svendsen et al., "Impact of Soft Tissue on In Vivo Accuracy of Bone Mineral Measurements in the Spine, Hip, and Forearm: A Human Cadaver Study", Journal of Bone and Mineral Research, vol. 10, No. 6, 1995, pp. 868–873.

Ruegsegger et al., "Standardization of Computed Tomography Images by Means of a Mateial–Selective Beam Hardening Correction", Journal of Computer Assisted Tomography, 2:184–188, Apr., 1978.

Kuiper et al., "Accuracy and the Influence of Marrow Fat on Quantitative CT and Dual–Energy X–ray Absorptiometry Measurements of the Femoral Neck in Vitro", Osteoporosis Int. (1996) 6:25–30.

Fujii et al., "Comparison of Trabecular Bone Density at Vertebral and Radial—Sites Using Quantitative Computed Tomography", Osteoporosis Int. (1996) 6:486–490.

Grampp et al., "Assessment of the Skeletal Status by Peripheral Quantitative–Computed Tomography of the Forearm: Short–Term Precision In Vivo and Comparison to Dual X–Ray Absorptiometry", Journal of Bone and Mineral Research, vol. 10, No. 10, 1995, pp. 1566–1576.

Wu et al., "Bone Mineral Crystal Properties Studied by Solid State $^{31}P$ $T_2$ Relaxation", Proceedings, $4^{th}$ Annual Meeting, International Society for Magnetic Resonance in Medicine, New York, NY, Apr. 27–May 3, 1996, p. 1079.

* cited by examiner

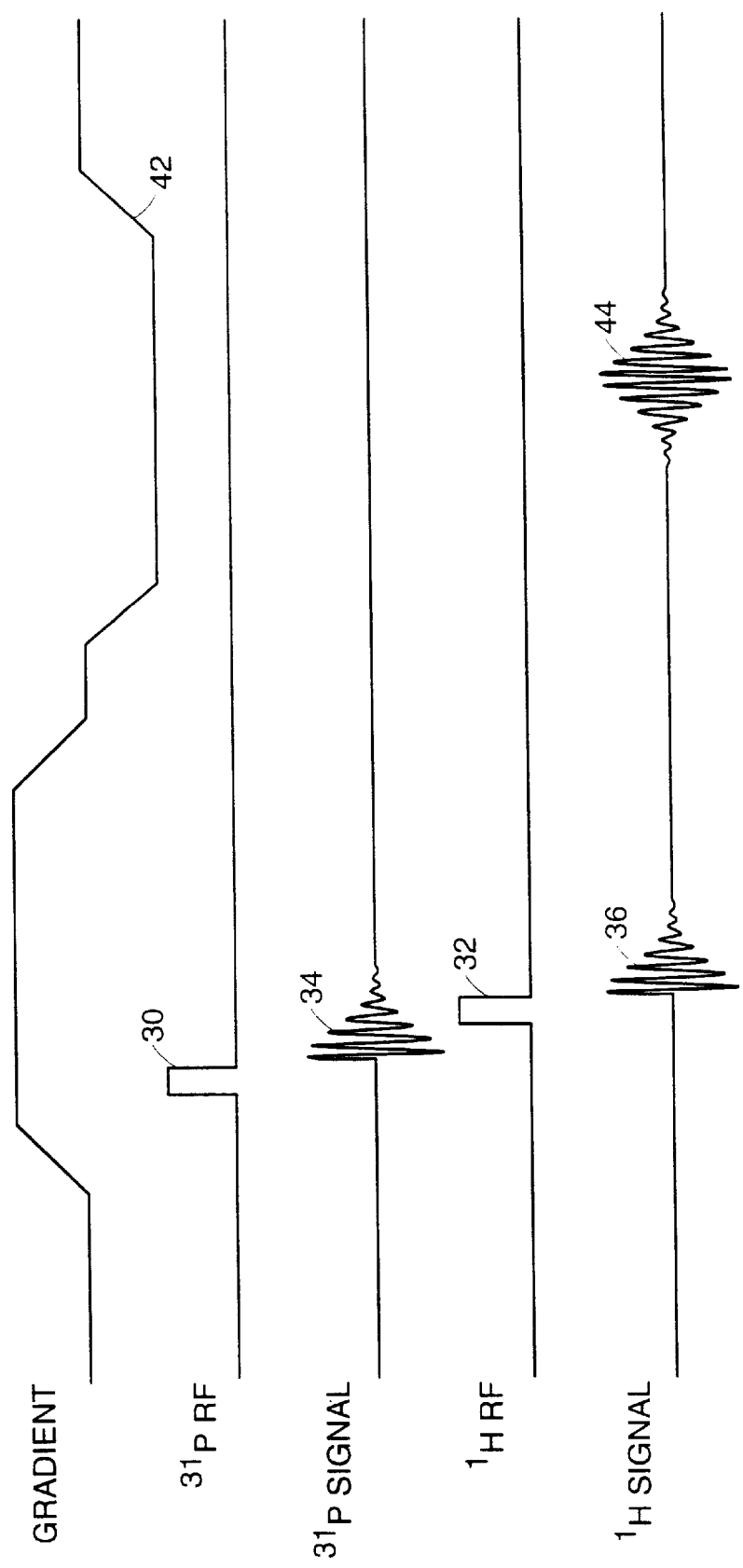

SOLID-STATE MAGNETIC RESONANCE IMAGING

BACKGROUND OF THE INVENTION

The bones of a skeletal system have a dense outer shell, or cortex, made of cortical bone (alternatively termed "compact" or "dense" bone). Inside the cortex, many types or regions of bone also have a mesh or network of trabecular bone (alternatively termed "spongy" or "cancellous" bone), made up of roughly the same material as the cortical bone. The region or regions enclosed by the cortex and/or the trabecular network contain marrow, and are aptly termed the "marrow space." In other types or regions of bone, particularly long bones such as femurs, the cortical bone encloses a trabecular-free marrow space, termed the "medulla" or the "medullary cavity." Regardless of whether it is contained in the trabecular network or the medullary cavity, marrow is comprised of living matter, including cells and a circulatory system, that supports the living constituents of the bone. Marrow also contains fat, and houses certain components of the blood-forming and immune systems of the body.

The dense bone material that makes up the cortical and trabecular bone is a composite material, made up of organic and inorganic constituents, intimately mixed. The organic constituents are alternately termed the "matrix" or "osteoid," and are comprised primarily of the protein collagen. The matrix is cartilage-like and flexible, and gives the bone material elasticity arid toughness.

The inorganic constituents are extremely small mineral crystals, carried and bound into a cohesive mass by the matrix, and give the bone its hardness and compressive strength. The crystals are typically flat plates on the order of hundreds of Angstroms or less on a side, and tens of Angstroms in thickness. The mineral crystals comprise about 60 to 70 percent of the total dry weight of dense bone.

A healthy human skeletal system among other things structurally supports the body, provides a set of levers for the mechanical actions of the skeletal muscles, protects the internal organs, houses parts of the blood-forming and immune systems, and functions as a storage reservoir for phosphate, calcium and other ions.

In an unhealthy skeletal system, one or more of these features may be compromised or lost. In the bone disease osteoporosis, the amount of bone in the skeleton is reduced, leading to weak and brittle bones and an increased risk of fracture. In Paget's disease, the rate at which bone mineral and matrix are cyclically resorbed (dissolved) and deposited is abnormally high, leading to distorted bone structure and pain. In osteomalacia (which is known as rickets when it affects growing children), there is an insufficient proportion of mineral to matrix. And in some instances, a bone fracture will not heal because of a failure in the bone reconstruction mechanism, a pathological condition known as nonunion.

SUMMARY OF THE INVENTION

In one aspect of the invention, an object comprising an isotope is subjected to a main magnetic field, as well as to a pulse sequence in which an RF excitation pulse is generated during a magnetic field gradient pulse. RF signals emitted by the excited isotope are acquired after the RF pulse, and then processed to generate data representative of the spatial distribution of the isotope within the object.

Because the magnetic field gradient pulse is initiated prior to the RF excitation pulse, the acquisition of the emitted RF signals can begin almost immediately following the conclusion of the RF excitation pulse. There is no need to wait for the gradient pulse to ramp up and stabilize, and/or for eddy currents to decay, after the RF pulse. This reduces the "deadtime" (the time during which the, e.g., analog-to-digital converter is unable to sample emitted RF signals) between the end of the RF pulse and the start of sampling. Reducing deadtime is an important consideration when imaging an isotope with a relatively short transverse relaxation time $T_2$, such as an isotope carried in solid-state in the object being imaged. If the gradient pulse were generated after the RF pulse, the MR signal from such solid-state isotopes might largely or entirely disappear by the time the gradient ramped up and stabilized. Initiating the gradient pulse prior to the RF excitation pulse further allows the gradient rise time to be relatively long (i.e., the rate of change of magnetic flux (dB/dt) to be relatively low), and thus guards against causing nerve stimulation in the subject being imaged. For example, the rise time can be on the order of 0.1 s, even when the $T_2$ for the isotope of interest (e.g., solid-state phosphorus-31 ($^{31}P$) in bone) is on the order of 100 $\mu$s.

Embodiments of this aspect of the invention include the following features. Two additional gradient pulses are generated, such that the three gradient pulses are mutually orthogonal, and define a gradient vector. All three gradient pulses are initiated prior to the RF excitation pulse, and the RF pulse is generated during the three gradient pulses (e.g., 200 $\mu$s after the gradient pulses rise to full amplitude). The acquisition of RF signals emitted by the excited isotope occurs during the generation of the three gradient pulses, and begins substantially immediately (e.g., less than 40 $\mu$s, preferably less than 20 $\mu$s, and more preferably less than 5 $\mu$s) after the conclusion of the RF excitation pulse.

The pulse sequence comprising the three orthogonal gradient pulses and the RF excitation pulse is executed a plurality of times, e.g., on the order of one thousand times. Each pulse sequence has an associated gradient vector. Although these vectors all have substantially the same magnitude, e.g., a value between 2 and 12 G/cm such as 9 G/cm, each vector has a unique direction.

Repeating this set of sequences permits signal averaging to increase the signal-to-noise ratio (SNR). If the entire set of about one thousand gradient vectors is repeated four times (i.e., if each vector is generated on four separate occasions), then there are about four thousand total acquisitions. The acquisitions can occur in any order.

To keep the total sampling time relatively short, the interpulse repetition time TR is less than about 1.0 s, more preferably less than about 0.5 s, and even more preferably less than about 0.3 s. The flip angle of the RF excitation pulse is less than about 30°, more preferably less than about 20°. Although this results in sampling only a portion of the longitudinal magnetization M, it permits shorter interpulse repetition times TR and improves signal-to-noise ratio for a fixed image scan time.

The acquired RF signals emitted by the excited isotope reside on radial lines in a spherical polar coordinate system in the k-space (the Fourier transform of the image), wherein the points in the spherical polar coordinate system can be represented by vectors k from the origin. In processing these data, each is multiplied by its associated $|k|^2$ (the square of the magnitude of k), and then interpolated onto a three-dimensional Cartesian grid before being subjected to Fourier transformation.

Processing the acquired RF signals further includes generating data representative of the density of the isotope, e.g., $^{31}P$ or $^{1}H$, in the object, e.g., a region or specimen of bone. In determining the spatial density of $^{31}P$ in a specimen of bone, a calibration phantom comprising a known density or densities of $^{31}P$ can be positioned near the bone and subjected to the main magnetic field and pulse sequence, such that the acquired RF signals can be processed to yield an image of both the bone specimen and the phantom. The $^{31}P$ density in the bone specimen can be assessed by comparing the intensity of the specimen image to the intensity of the phantom image.

In still other embodiments, RF excitation pulses can excite plural isotopes, e.g., $^{31}P$ and/or $^{1}H$, and RF signals emitted by both isotopes can be acquired and processed to generate data representative of the spatial distribution of either or both of the two isotopes within the object, e.g., spatial density data. The data sets can be compared and contrasted, e.g., to determine the density ratios of the two isotopes in the object.

In another aspect of the invention, an object comprising an isotope is subjected to a main magnetic field, as well as to a pulse sequence including an RF excitation pulse and a magnetic field gradient pulse. RF signals emitted by the excited isotope are acquired substantially immediately following the conclusion of the RF pulse, and then processed to generate data representative of the spatial distribution of the isotope within the object.

As noted, acquiring emitted RF signals substantially immediately (e.g., less than 20 μs, and preferably less than 5 μs) following the conclusion of the RF excitation pulse increases the time available for sampling the emitted RF excitation signals.

In another aspect of the invention, in vivo solid-state tissue is positioned in a substantially static magnetic field and subjected to magnetic gradients in at least two dimensions. Isotopes are excited in the solid-state tissue, and RF signals emitted by excited isotopes are acquired and processed to generate data representative of the distribution of the isotope within the solid-state tissue.

Among other advantages, this aspect of the invention permits complex, e.g., overlapping, solid-state bone structures such as the hip or hand to be directly imaged, in three dimensions, without the use of ionizing radiation. The data can be used for qualitative and quantitative analysis of the solid-state structures, e.g., to assess bone mineral density and/or degree of mineralization. In embodiments of this aspect of the invention, RF signals for generating a three-dimensional image of the distribution of the isotope within the solid-state tissue are acquired in less than about 35 min., preferably less than about 25 min.

In another aspect of the invention, a bone specimen is positioned in a substantially static magnetic field and subjected to magnetic gradients in at least two dimensions. An isotope (e.g., $^{31}P$) is excited in the bone, and RF signals emitted by the excited isotopes are acquired and processed to generate data representative of the spatial distribution of the isotope within the bone, which data is then itself processed (e.g., by evaluating its intensity) to determine the mineral density of the bone.

Bone mineral density (BMD) is an important quantitative diagnostic measurement in assessing skeletal health. BMD can facilitate the clinical diagnosis of disorders including osteoporosis and rickets, and is a principal factor affecting a subject's risk of bone fracture or nonunion. The ability to assess BMD without either destructive testing (such as biopsy) or subjecting the subject to ionizing radiation (such as x radiation) allows for relatively frequent BMD diagnosis of relatively broad scope in terms of the number and variety of skeletal regions examined.

In preferred embodiments of this aspect of the invention, a phantom is subjected to magnetic gradients along with the bone. The phantom includes at least two different densities of $^{31}P$, and the RF signals acquired during imaging are processed to show the spatial distribution of $^{31}P$ in the phantom as well as in the bone sample. The intensity of the data representative of the bone is compared to the intensity of the data representative of the phantom.

In another aspect of the invention, an object comprising two different compounds, each including an isotope (it may be the same isotope in both compounds), is positioned in a substantially static magnetic field. The isotope in one of the compounds has a different spin-lattice relaxation time $T_1$ in the static magnetic field than the isotope in the other compound. The object is subjected to an RF excitation pulse sequence that excites the isotopes in both compounds, and RF signals emitted by the excited isotopes are acquired. From these acquired signals, a data set representative of the distribution of substantially only one of the compounds within the object is obtained.

In preferred embodiments of this aspect, a data set representative of the distribution of substantially only the other one of the compounds within the object is also obtained. The RF excitation pulse sequence comprises two series of RF excitation pulses, with different flip angles, interpulse repetition times, or both. The data sets are obtained by processing the acquired RF signals in accordance with the spin-lattice relaxation times, and one or both of the flip angles and interpulse repetition times. By increasing the number of RF excitations appropriately and employing mathematical techniques such as the computation of linear combinations of the data sets, this technique can also be employed to generate separate images of the distributions of more than two compounds in the object.

Being able to discriminate in this manner between different compounds offers a non-invasive way to study and analyze the interplay between the different compounds, e.g., over time. For instance, if an implanted prosthesis includes one or more compounds containing $^{31}P$, this technique permits the prosthesis and the bone to be imaged independently, or collectively, e.g., to study and analyze the remodeling of bioactive synthetic materials in vivo.

Other features and advantages of the invention will be apparent from the description of the preferred embodiments, and from the claims.

BRIEF DESCRIPTION OF THE DRAWINGS

FIG. 8 is the timing diagram shown in FIG. 6, with an inversion gradient vector to generate a gradient-echo signal.

DESCRIPTION OF PREFERRED EMBODIMENT(S)

1. The System

Figure 1:
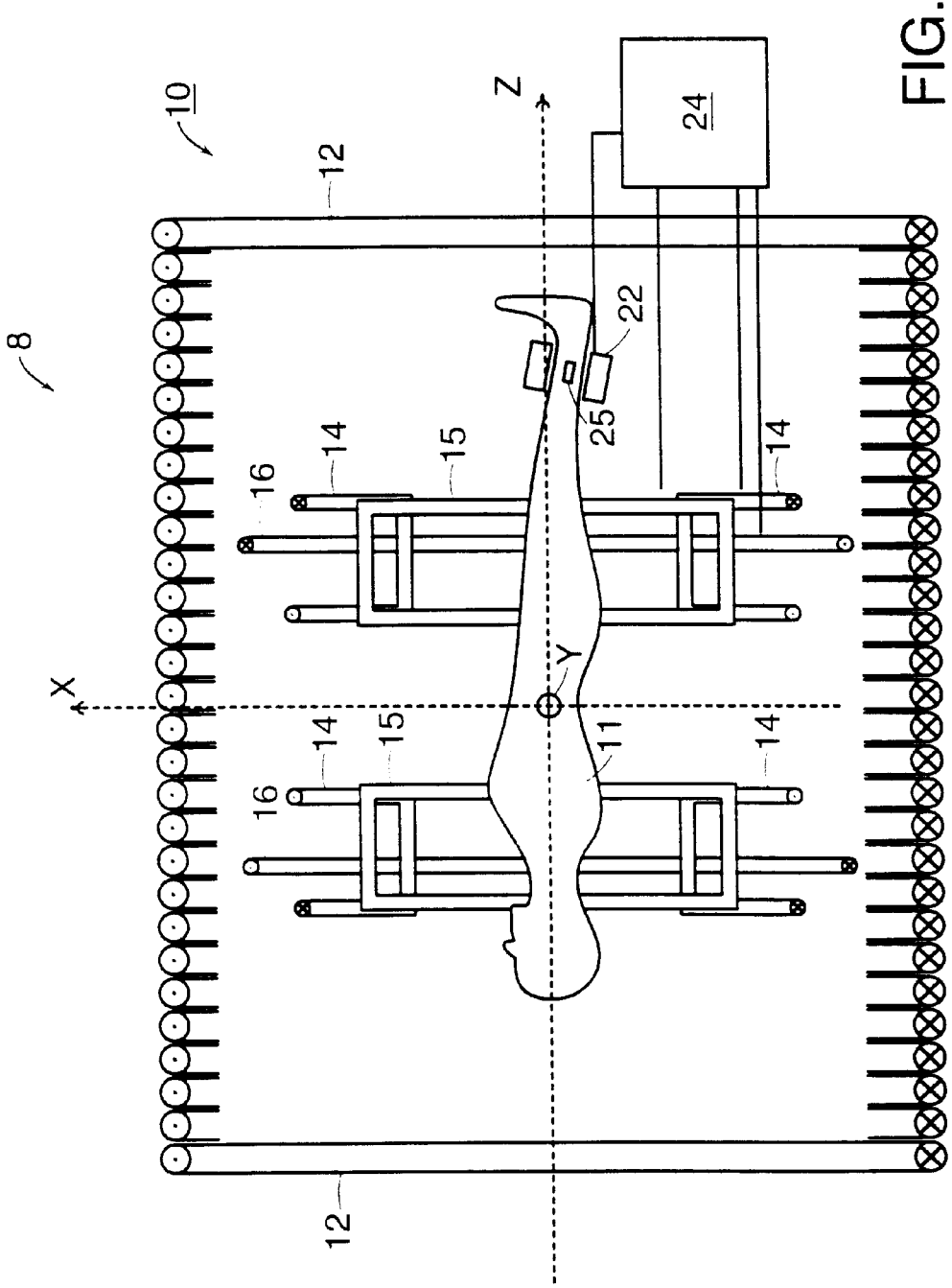
FIG. 1 is a cross-sectional, diagrammatic view of an arrangement of MRI coils around a subject body.

As shown in FIG. 1, a magnetic resonance imaging (MRI) system 8 includes a set of electromagnetic coils 10 surrounding a subject 11. Although subject 11 is shown in FIG. 1 to be an entire person, it could instead be a limb or region of a person, or a nonliving object. As explained in detail below, the MRI system 8 facilitates and enables the imaging and analysis of isotopes carried in, e.g., hard tissues such as bone ("solid-state imaging").

The set of electromagnetic coils 10 includes a main coil 12 and three orthogonal gradient coils 14, 15, 16, respectively oriented in relation to orthogonal x, y, and z axes.

The main coil 12 is a superconducting magnet that generates a static magnetic field, e.g., a 2.0 Tesla (T) magnet with an 18 cm bore (available from Nalorac Corp., Martinez, Calif.), or a 4.7 T magnet with a 30 cm bore (available from Oxford Instruments, Oxford, U.K.).

Each of the gradient coils 14, 15, 16 generates a magnetic field gradient $G_x$, $G_y$, or $G_z$ in its respective x, y, and z gradient coil direction. In the 2.0 T system, the gradient coils generate up to, e.g., a 12 G/cm magnetic field gradient (gradient coils and the power supplies that drive them available from Oxford Instruments). In the 4.7 T system, the gradient coils generate up to, e.g., a 9 G/cm magnetic field gradient (gradient coils available from General Electric; the power supplies that drive them available from Techron).

Figure 2:
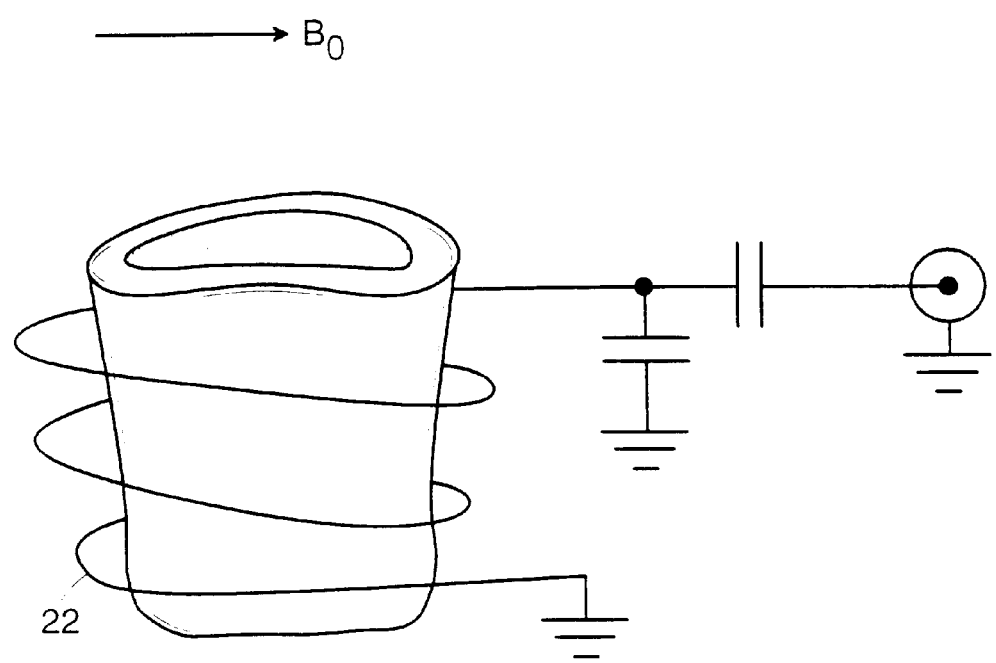
FIG. 2 is view of a radio frequency (RF) coil.
Figure 3:
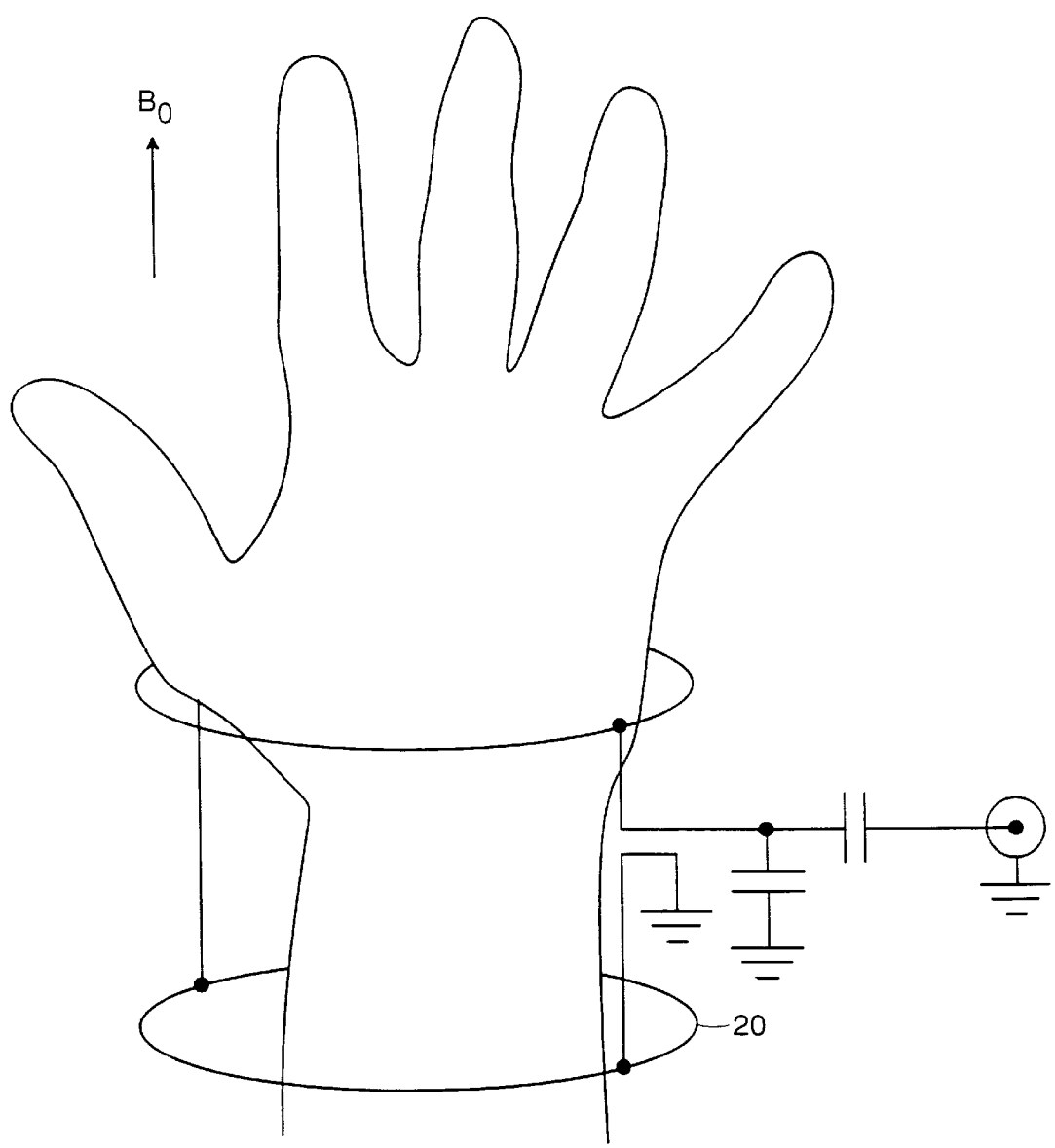
FIGS. 3 and 4 are views of other RF coils.
Figure 4:
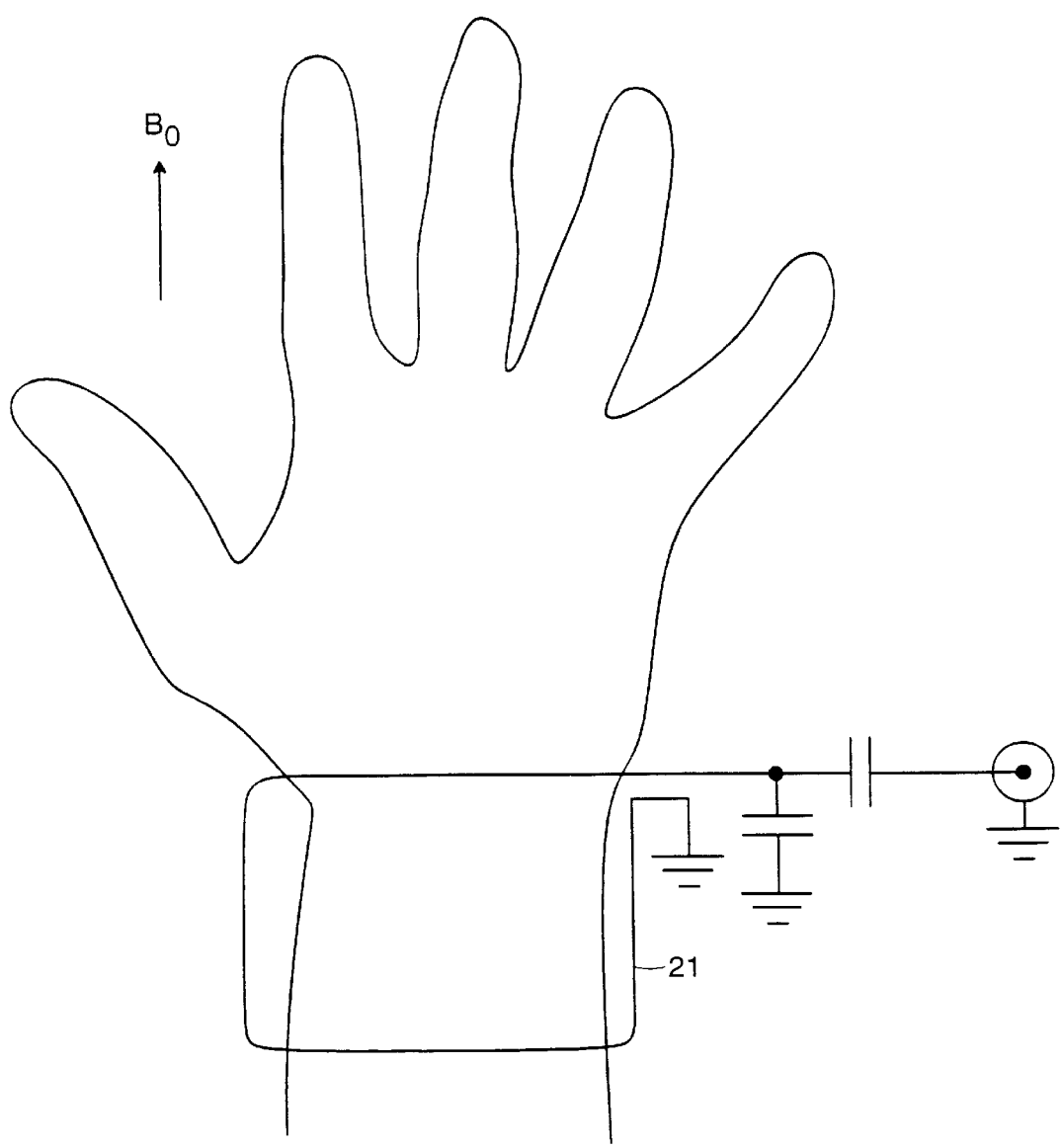

A radio frequency (RF) coil 22 positioned around or near the site to be imaged generates RF excitation pulses that excite isotopes within the site, and also detects RF signals emitted by the excited isotopes. The RF coil 22 in the 2.0 T system, shown in FIG. 2, is, e.g., a 2.7 cm long by 3.3 cm diameter single-tuned solenoidal coil. The RF coil in the 4.7 T system is, e.g., a single- or double-tuned surface coil. Other RF coils 20, 21 are illustrated in FIGS. 3 and 4.

A console 24 drives and receives signals from the magnetic field gradient coils 10 and the RF coil 22. The 2.0 T system uses, e.g., a SISCO/Varian (Palo Alto, Calif.) console, and the 4.7 T system uses a Bruker Instruments (Fremont, Calif.) Omega console.

A calibration phantom 25 can optionally be positioned at or near the region of interest of the subject 11, such that it will appear in the final image. The calibration phantom 25 has a known magnetic resonance behavior, and includes material having the same isotope being imaged in the subject. For instance, if the MRI system is configured to image $^{31}P$ in the bones of the subject, the phantom 25 can include a $^{31}P$ compound of one or more known densities ρ. For instance, the phantom 25 can be an acrylic cylinder 2.54 cm. in diameter and 2.56 cm in length with four precision-milled right circular cylindrical holes, each containing a mixture of hydroxyapatite powder $Ca_{10}(OH)_2(PO_4)_6$ (available from Aldrich, St. Louis, Mo.) diluted with silicon dioxide (available from Johnson Matthey, Seabrook, Me.). Each cylinder contains a different density of hydroxyapatite, e.g., 1.08, 0.86, 0.54, and 0.30 g/cm$^3$.

2. The Pulse Sequence

In the magnetic resonance of solids, the "spin-spin," or "transverse," relaxation time $T_2$ tends to be extremely short when compared to fluid-state magnetic resonance. $T_2$ is the exponential time constant that characterizes the time in which the magnetic resonance signal irreversibly decays following excitation. Thus, $T_2$ reflects the time available to encode spatial information in the signal, as well as to detect the signal, as described in further detail below.

The relatively short transverse relaxation time $T_2$ that characterizes solid-state magnetic resonance is attributable to "direct-dipole," or "spin-spin" coupling between and among the nuclear spins in the excited specimen. Each nuclear spin in the specimen, whether or not its signal is being detected by the MR instrument, is itself a microscopic magnet, generating a dipolar magnetic field (the shape of the field generated by a short linear magnet, such as a compass needle). Every nucleus in the specimen thus experiences not only the magnetic field generated by coils 10, but also the magnetic field of every other nucleus in the specimen. However, the intensity of these dipolar fields falls off as the inverse cube of the distance between the nuclei, and so the effect is predominantly local; only those nuclear spins within a distance of a few atomic diameters affect the total magnetic field experienced by a given nucleus.

The totality (vector sum) of magnetic fields arising from neighboring nuclei in the specimen at a particular nuclear site is called the "local field," and is given the designation $B_L$. $B_L$ is a statistical quantity, since its specific magnitude and direction vary from site to site in the specimen. Although the average value of $B_L$ is normally zero, its mean square average in a solid material is nonzero (and is usually different for different isotopes in a specimen, e.g., $^1H$ versus $^{13}C$).

Because the specific value of the local field $B_L$ in a solid specimen varies from site to site, the Larmor (resonance) frequencies also vary from site to site, and so the presence of a local field with a relatively large mean square average indicates that there is a large spread in Larmor frequencies, and thus a relatively broad linewidth, throughout the sample. This is equivalent to a short $T_2$. For instance, a typical magnetic resonance instrument employs a magnetic field strength $B_0$ in the range of about 1–10 T (10,000–100,000 Gauss, G). Local fields in solids are approximately in the range of 1–10 G, giving spectral linewidths in the range of 1–50 kHz and $T_2$'s in the range of 10–1000 µs, although the specific values depend on the particular nuclear species present and their spatial arrangement in the crystal lattice of the solid. By contrast, molecules in a fluid specimen are in rapid and isotropic motion. The local fields thus average to zero, and the contribution to spin-spin coupling effectively disappears.

In addition to the dipole-dipole interaction, there are other interactions experienced by nuclear spins in solids that contribute to line broadening (shortened $T_2$), as well as to increases in spin-lattice relaxation times $T_1$. These interactions include chemical shift anisotropy and quadrupole coupling.

As a result of these influences, the $T_2$ for solid-state phosphorous-31 ($^{31}P$) in bone in a 2.0 T field is on the order of 100 µs. In order to image this material with spin- or gradient-echo techniques, the minimum echo time (TE) would have to be on the order of or shorter than this $T_2$ for sufficient spin-echo or gradient-echo signal to be detected. This would involve switching relatively large gradient fields at relatively high frequencies. This would require high-bandwidth power supplies, and could result in nerve stimulation in the subject 11.

Figure 5:
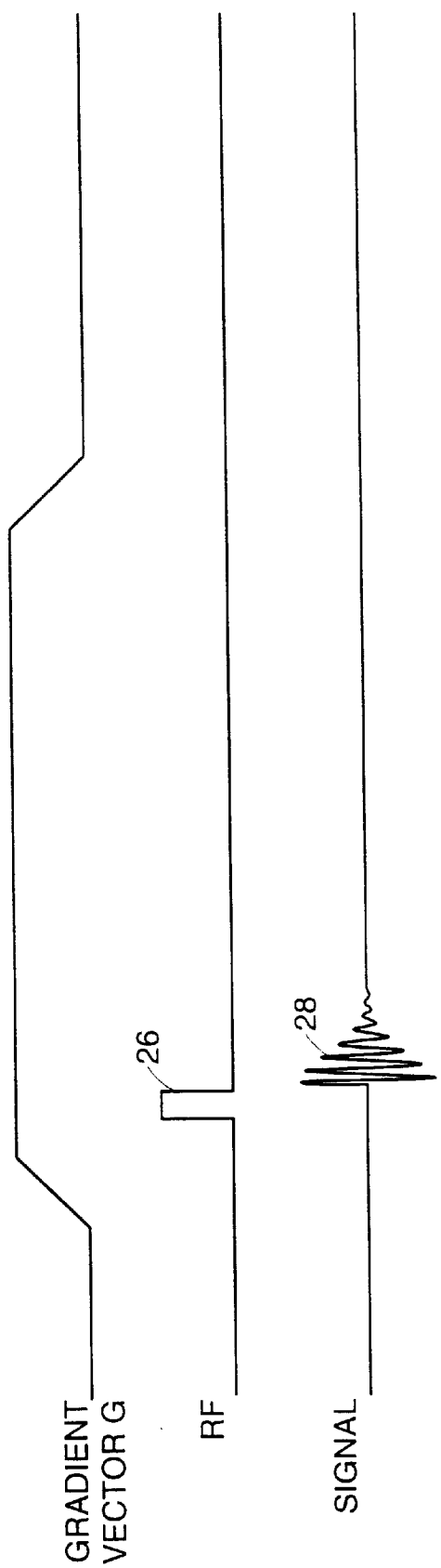
FIG. 5 is a timing diagram showing signals used in a solid-state imaging sequence.

Alternatively, the spin or gradient echo can be eliminated from the pulse sequence by instead acquiring a free induction decay (FID) signal. A pulse sequence that enables the FID of the excited isotopes to be sampled is shown in FIG. 5. During a complete image scan, the FIG. 5 pulse sequence is repeated, e.g., 4096 times.

The FIG. 5 pulse sequence is initiated by the console 24, which drives the gradient coils 14, 15, and 16 to generate three gradient pulses $G_x$, $G_y$, and $G_z$ in the respective x, y, and z directions, yielding a gradient vector G. The magnitude of the gradient vector G remains substantially constant (except for the rise, settling, and fall times) throughout the FIG. 5 pulse sequence, at a value in the range, e.g., 2–12 G/cm. These gradients are higher than the maximum 1–2 G/cm typically used in clinical MRI in order to enhance spatial resolution in the face of the broadening effects of the short $T_2$. In view of the relatively high magnitude of the gradient vector G, the rise and fall times of the gradient pulses $G_x$, $G_y$, and $G_z$ are chosen to be fairly long, on the order of 0.1 s. This guards against nerve stimulation in the subject 11, which is primarily a function of the rate of change of magnetic flux (dB/dt), as opposed to the steady state magnitude or gradient of the field. Because the gradient pulses $G_x$, $G_y$, and $G_z$ are initiated before the RF excitation pulse 26, this relatively long rise time does not reduce the total available sampling time. If the gradient pulses were generated after the RF pulse, the MR signal from the solid-state isotopes would entirely or largely disappear by the time the gradients ramped up and stabilized.

After the 0.1 s rise time for the gradient pulses $G_x$, $G_y$, and $G_z$, the console 24 waits 200 μs before generating the RF excitation pulse 26. This delay permits the gradients to stabilize, and any eddy currents induced, e.g., in the electrically conductive structures of the coil and/or magnet, to decay.

The RF excitation pulse 26 is a single, rectangular hard pulse having a frequency at or near the nominal Larmor frequency of the chemical specie of interest. For instance, the Larmor frequency of $^{31}P$ is 34.27 MHz at 2.0 T, and that of $^1H$ is 84.67 MHz.

The other parameters of this pulse (i.e., the flip angle and the duration) are a function of the desired quantitative accuracy, signal-to-noise ratio, and total image acquisition time.

The isotopes carried in, e.g., hard tissues such as bone characteristically have relatively long spin-lattice relaxation times $T_1$. For instance, the $T_1$ for solid-state phosphorous-31 ($^{31}P$) in ex vivo bone in a 2.0 T field is on the order of 5–20 s, and in in vivo bone in a 1.5 T field is on the order of 5–7 s. After a 90° RF excitation pulse, resulting in complete saturation, a 95 percent recovery of the longitudinal magnetization takes three $T_1$ intervals, and a 99 percent recovery takes five $T_1$ intervals. If the interpulse repetition time TR is selected to equal five $T_1$ intervals in order to achieve 99 percent accuracy, then a total image scan of 4096 FIDs would take almost 5 days.

Total image scan time can be reduced by using flip angles β of less than 90°. Although this results in sampling only a portion of the longitudinal magnetization M, it permits shorter interpulse repetition times TR and improves signal-to-noise ratio for a fixed image scan time.

TR is selected such that a complete image can be scanned (e.g., 4096 FIDs) in a length of time acceptable to the subject 11. For example, TR can be set to 0.3 s, giving a total imaging time of on the order of 20 min. $T_1$, along with the equilibrium value of the longitudinal magnetization $M_0$ and the pre-exponential constant α (equal to 2 under ideal conditions), can be determined using an inversion recovery pulse sequence (comprising a 180° RF pulse, followed by a delay of duration τ, followed by the FID sequence shown in FIG. 5) and a three-parameter nonlinear least squares fit to the model:

$$M = M_0 \, (1 - \alpha e^{-\tau/T_1}) \tag{1}$$

The steady-state relationship between flip angle β, longitudinal magnetization M, the equilibrium value of the longitudinal magnetization $M_0$, TR and $T_1$ in the pulse sequence of FIG. 5 can be expressed as:

$$M = M_0 \frac{(1-E)\sin\beta}{1-E\cos\beta} \tag{2}$$

where:

$$E = e^{-TR/T_1} \tag{3}$$

For any given TR and $T_1$, the optimum signal-to-noise ratio is obtained with $\beta_{opt}$:

$$\beta_{opt} = \cos^{-1}(E) \tag{4}$$

Once a convenient pulse duration is chosen, the flip angle is computed using equation (4) to obtain optimum signal-to-noise ratio. For instance, when imaging bone with a $T_1$ of about 20 s in the 2.0 T system, a 10° RF excitation pulse 26 can be used, along with a TR of 0.3 s, resulting in a time of 23 min. for a complete image scan of 4096 FIDs. (The exact duration calculation yields 20.5 min., but the scanner introduces small additional delays totalling 2.5 min.) Because $T_1$ increases in the stronger field (e.g., to about 30 s), a 10° RF excitation pulse 26 and a TR of 0.45 s can be used for a 4.7 T field, resulting in a time of 31 min. (neglecting delays attributable to the scanner), for a complete image scan of 4096 FIDs.

As shown in FIG. 5, in view of the relatively short $T_2$, (80 μs for $^{31}P$ in bone) sampling of the FID 28 begins substantially immediately after the end of the RF excitation pulse 26, e.g., after on the order of 40 μs or less, and preferably after on the order of only 5 μs or less. Sampling the FID substantially immediately after the end of the RF excitation pulse 26 reduces the time during which the relatively short solid state $T_2$ would cause signal dephasing and loss, improving SNR. Sampling the FID immediately after the pulse also minimizes variation of signal intensities in the resulting image due to variation in $T_2$ in different regions of the specimen. This helps preserve the quantitative accuracy of the image, by reducing $T_2$ weighting. Samples are collected at constant time intervals, with a total of 256 samples being collected during each FID.

As noted, scanning a complete image involves sampling, e.g., 4096 FIDs. The magnitude of the gradient vector G is the same in each FIG. 5 pulse sequence, e.g., a value in the range of 2–12 G/cm. Each set of 256 samples for each gradient vector G can be described in the Fourier domain (or "k-space") as a series of samples emanating from the origin. Specifically, the wave vector k=γGt follows a radial traversal of the Fourier space under the influence of the gradient vector G at time t during acquisition of a signal.

During a single typical imaging sequence, gradient vectors G are generated in 998 unique directions, and each gradient vector G is sampled four times to improve the signal-to-noise ratio. That is, over the course of collecting data for a single image, each combination of gradient pulses $G_x$, $G_y$, and $G_z$ is generated on four separate occasions. The data collected during these four "repeat" scans are averaged and stored in a data matrix. It is not necessary to turn off the gradient pulses $G_x$, $G_y$, and $G_z$ between successive pulse sequences to bring the magnitude of the gradient vector G to zero.

The 998 unique gradient vector directions fit conveniently into a pattern of 14 latitude rings about the unit sphere; the gradient pulses $G_x$, $G_y$, and $G_z$ are selected such that the 998 directions are distributed isotopically throughout the spherical k-space. Thus, only 4×998 (or 3992) of the 4096 FIDs are used to reconstruct the image. The data from the remaining 104 FIDs can be discarded, or can be used to measure the Larmor frequency, the receiver noise level, the receiver baseline offset, and/or similar properties. The full 4096 FIDs are nonetheless collected, because it is generally more convenient for computer hardware and software purposes to work with blocks of data in multiples of powers of 2. A lower number of gradient vector directions results in a lower image acquisition time, but lower spatial resolution, and a higher number of gradient vector directions results in a higher spatial resolution, but greater image acquisition time.

3. Data Processing

Following acquisition, a three-dimensional image can be reconstructed from the spherical stored data D(k) using projection reconstruction techniques. Details of image reconstruction techniques are disclosed in the following references, incorporated herein by reference: C. W. Stearns, D. A. Chesler, and G. L. Brownell, "Three Dimensional Image Reconstruction In The Fourier Domain," *IEEE Trans. Nucl. Sci.*, NS-34(1):374–378 (1987); C. W. Stearns, D. A. Chesler, and G. L. Brownell, "Accelerated Image Reconstruction For A Cylindrical Positron Tomograph Using Fourier Domain Methods," *IEEE Trans. Nucl. Sci.*, NS-37(2):773–777 (1990); D. A. Chesler et al., "Rapid 3-D Reconstruction From 1-D Projections For Metabolic MR Imaging of Short $T_2$ Species," *Society Of Magnetic Resonance*, Berlin (1992).

Step A. The stored data are first multiplied by $|k|^2$ (the square of its 1–256 sample number) to compensate for the nonuniform density of the data in the k-space. That is, since the 256 data points on each projection were sampled at constant time intervals, the locus of data points can be described as a series of concentric spheres, each pair of adjacent spheres being radially spaced apart by the same distance x, a constant determined by the sampling interval. Thus, the 998 data points on the outermost sphere with a radius of 256x have a much lower density than the 998 data points on the innermost sphere with a radius of only 1x.

Step B. The weighted data are then "interpolated," or "blurred," onto a regular $64^3$ Cartesian cubic reconstruction lattice. Specifically, each sampled data point is blurred from its true position in k-space to the eight surrounding points of the $64^3$ cubic reconstruction lattice. This is accomplished by adding a numerical value to each cubic reconstruction lattice point that reflects the numerical value of the true data sample, as well as the proximity of the true k-space position of the true data sample to the reconstruction lattice point. The reconstructed $64^3$ lattice corresponds to a field of view (FOV) of 4 cm$^3$, and a voxel size of 0.625 mm$^3$, although the spectral line width of the bone signal and the point spread function of the reconstruction procedure limit the actual linear spatial resolution to about 2 mm$^3$.

Step C. A "correction lattice" is then formed from a correction set of spherical data D' (k), where the value of every data point D' (k) in the correction set is one. The correction lattice is formed by subjecting the spherical data D' (k) to the density-compensating (Step A) and blurring (Step B) steps described above for the true FID data D (k). Each point of the cubic reconstruction lattice is then divided by the corresponding point of the correction lattice.

Step D. The corrected cubic reconstruction lattice is then subjected to three-dimensional Fourier transformation.

Step E. To compensate for intensity distortions introduced by the blurring step, each point in the Fourier-transformed corrected cubic reconstruction lattice is divided by the corresponding value of a three dimensional sinc-squared function that varies as $[(\sin x \cdot \sin y \cdot \sin z)/(x \cdot y \cdot z)]^2$.

4. Data Analysis

The reconstructed image has a variety of diagnostic applications. It may be viewed to assess the distribution of the isotopes of interest in the subject 11. For instance, the principal component of bone mineral, a complex calcium phosphate, can be characterized as a poorly crystalline non-stoichiometric apatite similar to hydroxyapatite, $Ca_{10}(OH)_2(PO_4)_6$.

The chemical composition of bone mineral differs from hydroxyapatite in having less calcium, and by having ions not found in hydroxyapatite. More specifically, bone mineral is an apatitic calcium phosphate containing carbonate and small amounts of sodium, magnesium, fluoride, and other organic and inorganic trace components. This carbonated apatite, termed "dahllite," contains 4 to 6 percent carbonate by weight, and is also the mineral constituent of teeth and some invertebrate skeletons. Most of the phosphate ions in bone mineral are in the form $PO_4^{-3}$, but some may be protonated and have the formula $HPO_4^{-2}$. These protonated phosphate ions are referred to as hydrogen phosphate, acid phosphate, or biphosphate, and may be present in amounts up to about 15 percent of all phosphate ions. The term "orthophosphate" refers to the entire class of protonated and unprotonated phosphate ions derived from phosphoric acid, $H_3PO_4$.

Thus, the amount of $^{31}P$ in a region of bone is representative of the overall bone mineral density. The intensity of a reconstructed image of $^{31}P$ is therefore representative of the mineral density of the bone itself—there is no need to rely on assumptions about, or models of, tissue composition. The $^{31}P$ image is generated without ionizing radiation (such as X-rays), and can be used for qualitative and quantitative analysis of the often-complicated three-dimensional structure of a section of bone, especially trabecular bone, and/or of a number of overlapping bones or bone structures, such as in the hip or hand. Information on the chemical composition and the degree of mineralization of the matrix (i.e., the ratio of bone mineral to matrix) can also be obtained from the image if $^1H$ data are also obtained. Although $^{31}P$ is typically present also in the soft tissues surrounding the bone (e.g., in phospholipids and in solution metabolites such as PCr, ATP, $P_i$, etc.) the phosphorous concentration in bone is usually several orders of magnitude higher, and so the MR signal from the soft tissues does not interfere with the signal from the bone.

As noted, the assessment of the reconstructed image may be quantitative, as well as qualitative. Qualitatively, the image reveals the spatial distribution of the relative mineral density of the bone region in question, with brighter regions of the image corresponding to higher mineral densities than dimmer regions. This qualitative image can be normalized with respect to either a predetermined pixel intensity, or with respect to the intensity of a certain pixel or region of pixels. For instance, the mean pixel intensity over the entire image can be computed, and then the image intensity can be normalized on a pixel-by-pixel basis with respect to this mean pixel intensity.

One quantitative measurement of significance is bone mineral density (BMD). BMD is an important consideration in the clinical diagnosis of skeletal disorders, including osteoporosis and rickets, and is a principal factor affecting a subject's risk of bone fracture.

The equilibrium value of the longitudinal magnetization $M_0$, discussed above, is proportional to the mass of the isotopes of interest in the object being imaged; magnetization per unit volume is thus proportional to density. The longitudinal magnetization M is also proportional to the measured signal intensity, i.e., the intensity of the reconstructed image. In order to correct the observed longitudinal magnetization M to the true equilibrium value $M_0$, equation (2) above is inverted to provide:

$$M_0 = FM \quad (5)$$

where $$F = \frac{1 - E\cos\beta}{(1-E)\sin\beta} \quad (6)$$

The image intensity data can be converted to true density information using the image of the calibration phantom 25, as well as the known density(ies) of the calibration compound. Since the true density(ies) of the calibration compound(s) is/are uniform, the intensity(ies) of the phantom in the reconstructed image should also be uniform. The mean pixel intensity of a desired region of the image of the specimen is first found. The mean pixel intensity of a region of the calibration compound is then found. Dividing the mean pixel intensity of the specimen by the mean pixel intensity of the calibration compound yields the relative density of the specimen region (relative to the calibration compound density). Since the true density of the calibration compound is known, the true density of the region of the specimen can be determined by multiplying the relative density by the true density of the calibration compound. Where the calibration phantom includes compounds at more than one density, as is the case with phantom 25, a calibration curve mapping intensity versus true density can be generated using a least-squares fit of the phantom density and intensity values. This is explained in further detail below in connection with equation (7).

In some instances, however, RF field variations and other spatial inhomogeneities can cause nonuniform intensity throughout the FOV, and thus regions having the same isotope density can have different intensities in the resultant MR image. To account for this, the calibration process can be limited to the portion of the phantom that was subjected to substantially the same RF field strength as the region of interest in the bone.

Regions of comparable RF field strength in the FOV can be identified in an initial calibration in which a different phantom, large enough to fill or nearly fill the FOV, is positioned alone in the MRI system 8. This phantom is, e.g., completely filled with 85% phosphoric acid, $H_3PO_4$. The liquid acid gives absolute filling uniformity and a very high signal-to-noise ratio (SNR). The resultant $^{31}$P image, generated under substantially the same conditions as used to generate images of the specimen, is examined to locate at least two regions of comparable intensity. Because of the uniformity of the phantom, the regions of the FOV that correspond to these regions of the image were evidently subjected to substantially the same RF field strength.

The foreknowledge of the locations of these regions of substantially the same RF field strength is then used to determine the density of the specimen image using the image of the phantom 25. For instance, if the RF field strength at the region corresponding to slices 45–48 of the specimen image is within 2% of the RF field strength at the region corresponding to slices 25–28 of the phantom image, then the intensity information from slices 25–28 of the phantom image are used in the calibration.

The calibration process need not use all of the intensity information for each slice of the phantom or the specimen image. For instance, within each utilized slice of the phantom, image pixels with a signal magnitude less than three times the background noise standard deviation can be discarded, and only the remaining pixel intensities used in the density calculation. The signal intensity I of these pixels can then be used to construct a linear calibration curve, I versus the known densities ρ of the hydroxyapatite/silicon dioxide mixtures, with a least squares fit:

$$\rho = KI + a \quad (7)$$

where the constant term a corrects for the nonzero average of the noise in the magnitude images.

In addition to RF field strength variation, the calibration can also take account of differing magnetic resonance properties of the calibration phantom 25 on the one hand, and the specimen on the other, where these different properties affect image intensity. For instance, if in a $^{31}$P solid-state three-dimensional projection image the unknown specimen contains bone and the calibration specimen contains a synthetic calcium phosphate, such as hydroxyapatite, the spin lattice relaxation times $T_1$ of the two materials will differ, and the signal intensity produced by an equal density of phosphorus atoms in each material can also differ. A correction factor, either measured experimentally or computed knowing the values of $T_1$ for the respective materials, as well as the details of the pulse sequence timing, can be applied to further correct the result of the calibration calculation. For instance, the density of the specimen in the region of interest can be calculated by multiplying the observed intensity of the reconstructed image of the region of interest by F (from equation (6)) to correct for $T_1$ contrast, and also by K (from equation (7)) to account for the intensity-to-density mapping of the calibration phantom.

Additionally or alternatively, the spatial variation in intensity resulting from RF field variations can be corrected, e.g., in software, by first mapping the field variation using the phosphoric acid ($H_3PO_4$) phantom image generated in the initial calibration This map can then be used, along with $T_1$ contrast correction if necessary, to correct the intensity of subsequent images. These subsequent images can be of the specimen only, or can include a phantom such as phantom 25 in addition to the specimen.

Additionally or alternatively, calibration can be effected by measuring a series of images with appropriate variations in the pulse sequence timing parameters in order to compute the relaxation times from the series of images, from which the appropriate corrections can be determined and applied.

Comparison testing shows a high degree of correlation between calculating BMD from solid-state $^{31}$P imaging and three other techniques for calculating BMD. In one test, 2 cm long specimens were cut from the midshaft cortices of ~4 month old calf femora, as well as from ~6 month old lamb tibiae. A bovine trabecular specimen was also cut from the femoral head, and excluded cortex to maximize the accuracy of the gravimetric and chemical analyses, discussed in detail below. External soft tissues were completely dissected from the specimens, which were then dried at room temperature. All specimens retained their full complement of protein and fat, but had low water content.

The specimens were first analyzed using the above described MRI technique. The cortical specimens were imaged at 2.0 T, and the trabecular specimen at 4.7 T. The bovine cortical and lamb cortical specimens, as well as the hydroxyapatite phantom, were subjected to 10° RF pulses, and a TR of 0.3 s. The bovine trabecular specimen was subjected to a 21° RF pulse, and a TR of 2.0 s. The fitted (using equation (1)) $T_1$s for the bovine cortical and lamb cortical specimens were 17.1±0.4 (standard deviation) and 19.8±0.5, respectively, and 16.3±1.3 for the bovine trabecular and 0.26 for the hydroxyapatite. (Only three columns of the phantom were filled with hydroxyapatite for the cortical bone images, whereas all four were filled for the trabecular images.)

The specimens were then subjected to dual energy x-ray absorptiometry (DEXA or DXA), in which a pair of digital projection x-ray scans at two x-ray energies are subtracted to yield an image of the mass density, from which bone mineral content (BMC) can be determined. A QDR-1000 DXA Densitometer (available from Hologic, Waltham, Ma.) was calibrated with a Hologic hydroxyapatite anthropomorphic spine phantom. The bone specimens were placed on a precision milled block of acrylic plastic 3.81 cm thick to simulate the background scattering conditions of the DXA phantom, and scanned at a scan step of 0.1 cm. Total scan times were 6–7 min., and the scan speed was 0.73 cm/s. All DXA analyses were performed using the manufacturer's software.

The specimens were next subjected to gravimetric analysis. The specimens were weighed, coated in clear acrylic nail polish to prevent water absorption, and their volumes measured by water displacement.

Following volume measurement, the specimens were ashed in a HTF55322A 3 inch horizontal tube furnace controlled by a CC58114PC programmable digital controller (available from Blue M, Asheville, N.C.). The specimens were heated to 300° C. for 2 hours, and then to 600° C. for 16 hours. Little or no carbonate is lost at 300° C., and only small amounts of carbonate are lost at 600° C.

The dry ash of each sample was weighed, dissolved in 6 N HCl, and transferred to a volumetric flask. The crucible was washed with distilled water, which was then pooled into the volumetric flask up to the mark. The sample was divided into two aliquots. One was diluted in 0.5 percent (vol/vol) HCL containing 0.1% lanthanum oxide (wt/vol) and assayed for calcium by comparison to standard calcium solutions using a 603 atomic absorption spectrophotometer (available from Perkin-Elmer, Norwalk, Conn.). To analyze for phosphorous, the second aliquot was dried by evaporation using a speed vacuum concentrator. 2.0 ml of distilled water and 0.5 ml of 10 N sulfuric acid were added to the dry residue, and the solution heated in a 150–160° C. oven for 3 hours. Two drops of 30% hydrogen peroxide were added, and the solution was returned to the oven for at least 1.5 hours more to complete the combustion and to decompose all of the peroxide. 4.6 ml of 0.22% ammonium molybdate and 0.2 ml of Fiske-SubbaRow reagent were added, mixed thoroughly, and heated for 7 min. in a boiling water bath, with marbles covering the tube. The optical density at 830 nm was recorded in a Perkin-Elmer Lambda 3 spectrophotometer. Phosphorous content was determined by comparison to standard phosphorous solutions. The mineral content of each specimen was calculated from the calcium and phosphorous analyses on the basis of Ca+PO$_4$.

The results of these techniques are summarized in Table 1 below. For comparison purposes, the BMC values from the DXA test were divided by the volume of the specimens as determined in the gravimetric analysis. In in vivo testing, the volume of the region of interest typically cannot be measured directly. The DXA system instead divides the BMC by the projection area of the DXA image to compute areal concentration (density in, e.g., g/cm$^2$).

TABLE 1

| Technique | Bovine Cortical (g/cm$^3$) | Lamb Cortical (g/cm$^3$) | Bovine Trabecular (g/cm$^3$) |
|---|---|---|---|
| MRI 3D BMD (T$_1$ Corrected) | 1.09 | 1.00 | 0.155 |
| DXA 3D BMD (DXA BMC/volume) | 1.08 | 1.07 | 0.208 |
| Gravimetry BMD (mass/volume) | 1.10 | 1.06 | 0.140 |
| Chemical Analysis BMD | 1.13 | 1.10 | 0.122 |

The solid-state MRI technique disclosed herein can also be used to discriminate between and analyze different compounds of the same isotopes. For instance, there are molecular structural differences between bone and synthetic hydroxyapatite. As noted above, these differences translate into very different T$_1$s for the two compounds: on the order of 20 s for ex vivo bone, on the order of 7 s for in vivo bone, and on the order of 0.5 s for synthetic hydroxyapatite.

T$_1$ "weighting" can be introduced by altering the pulse repetition time TR, the RF pulse flip angle, or both. Thus, a first image of a region containing both bone and hydroxyapatite can be obtained at, e.g., a TR of 0.3 s, and a flip angle of 20°. This image would show both the bone and the hydroxyapatite. A second image can then be obtained, e.g., a TR of 0.3 s, and a flip angle of 90°. At the larger flip angle, the signal from the bone is nearly saturated because of its higher T$_1$. However, the signal from the hydroxyapatite is not, so the resultant second image is substantially just of the synthetic material. The raw images can, e.g., be digitally subtracted on a pixel-by-pixel basis to show just the bone material. By increasing the number of images taken, this technique can also be used to discriminate between three or more different compounds in the same region that all contain the same isotopes (e.g., $^{31}$P) , but exhibit different T$_1$s.

One application for this T$_1$ weighting technique is to discriminate between bone and implanted prostheses, e.g., that include one or more compounds of $^{31}$P. This offers a non-invasive way to study and analyze the remodeling of bioactive synthetic materials in vivo. Other applications may include differentiating between and among bone mineral at various stages of maturity, bone at different stages in the remodelling cycle (in which bone material is cyclically resorbed (dissolved) and deposited), and bone under various conditions of pathology. For instance, the concentration of one of the minor constituent ions of bone mineral, HPO$_4^{-2}$, evidently decreases over time as the mineral matures, thus serving as a marker of mineral maturity. Evaluation of this marker could yield diagnostically useful information for processes or disorders involving bone mineral turnover, including osteoporosis, Paget's disease, and the healing or failure to heal of bone defects such as fractures and tumor resections.

The solid-state MRI technique disclosed herein can also be used to study non-phosphorous bone chemistry, or the chemistry of other solids, in or from living or nonliving specimens. Any particle or substance with a magnetic moment and yielding a magnetic resonance signal is a candidate for detection using the foregoing techniques (including but not limited to $^1$H, $^3$He, $^{11}$B, $^{13}$C, $^{14}$N, $^{23}$Na, $^{27}$Al, $^{29}$Si, $^{129}$Xe, electrons, muons, ferromagnetic and antiferromagnetic materials).

Figure 6:
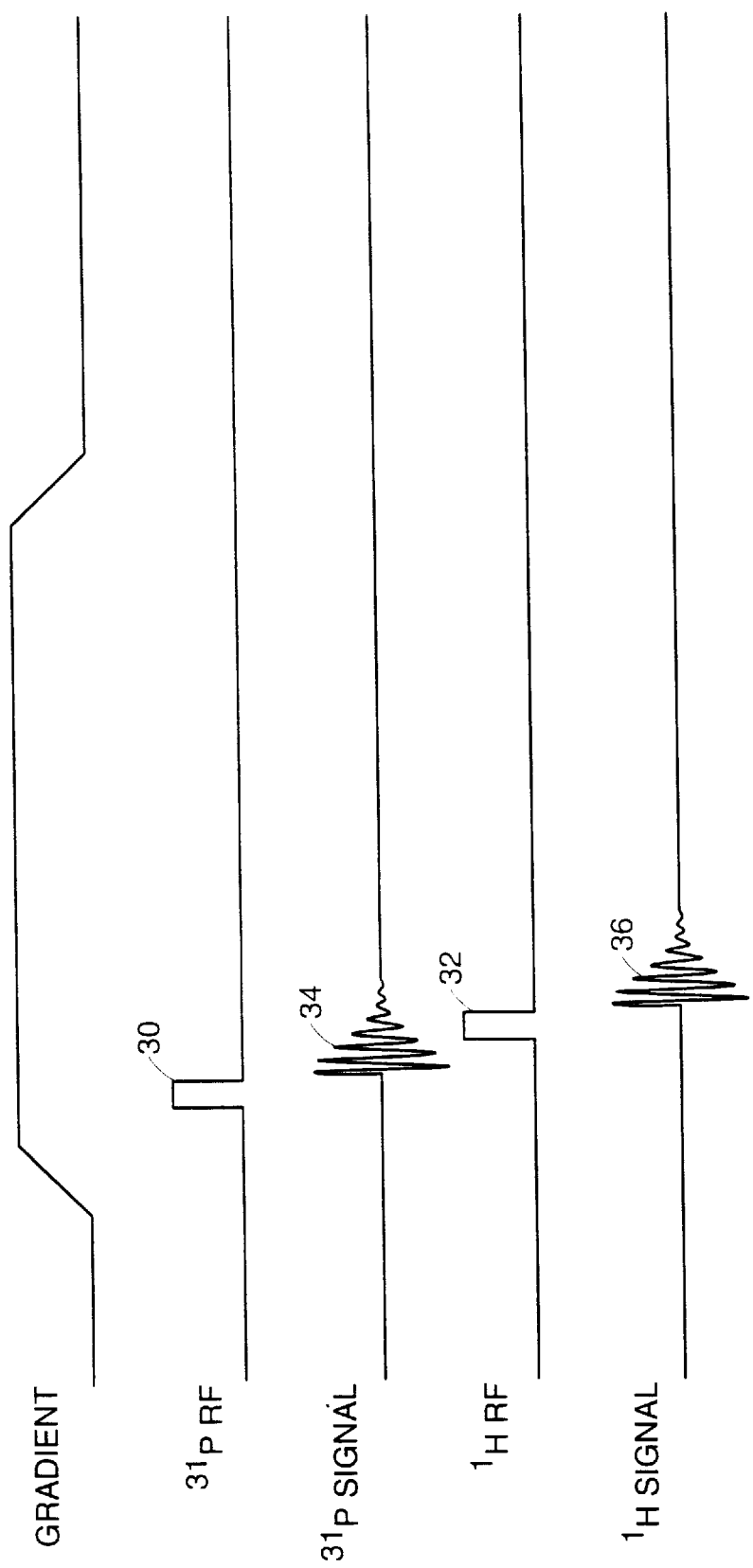
FIG. 6 is another timing diagram showing signals used in a solid-state imaging sequence.

For instance, a $^1$H image can be obtained as described above, or can be obtained simultaneously with a $^{31}$P image using, e.g., a double-tuned RF coil, tuned to both the Larmor frequency of $^1$H (84.67 MHz at 2.0 T), and that of $^{31}$P (34.27 MHz at 2.0 T). FIG. 6 shows a pulse sequence in which separate RF pulses 30, 32 respectively excite the $^{31}$P and $^1$H isotopes. The $^{31}$P and $^1$H FID signals 34, 36 from the coil can be processed separately, each set as described above, and the resultant images interleaved or otherwise processed. Although the RF excitation pulse for $^{31}$P is shown generated before the RF excitation pulse for $^1$H in FIG. 6, the order can be switched, or they can be generated simultaneously.

Figure 7:
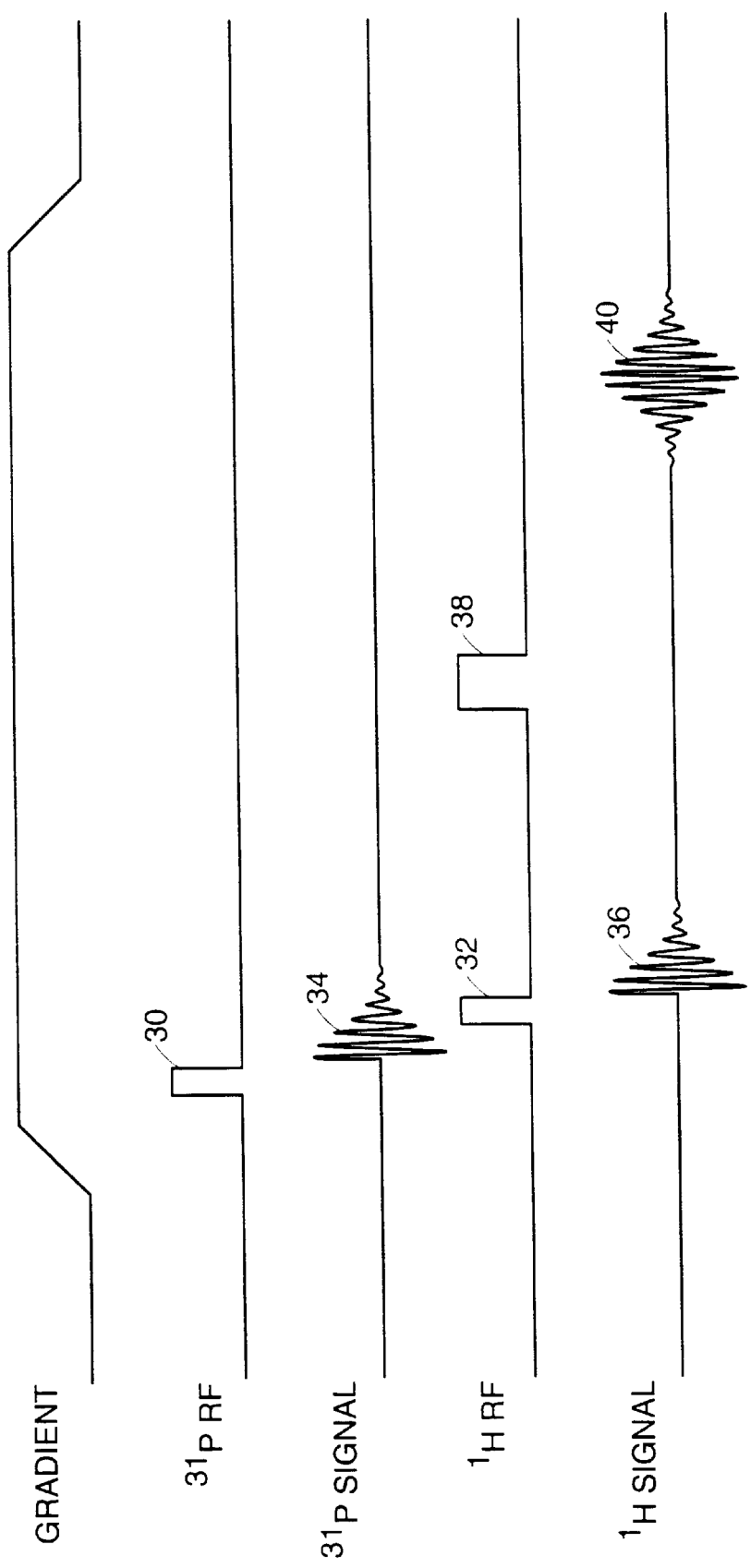
FIG. 7 is the timing diagram shown in FIG. 6, with an additional RF pulse to generate a spin-echo signal.

For instance, the images can be used to facilitate the in vivo determination of the mineral-to-matrix ratio, an important diagnostic indicator of skeletal health and integrity. Specifically, as noted above, the $^{31}$P image shows predominantly the BMD mineral concentration (the concentration of phosphorous in surrounding tissues being relatively low). The $^1$H image reconstructed from the $^1$H FID 36 shows all protons, those carried in the matrix as well as those carried in the marrow and the mineral, and can be termed "the total $^1$H image." To identify only the protons in the matrix and mineral, a fluid-state-only $^1$H image is generated using, e.g., spin-echo or gradient-echo techniques. A pulse sequence for generating a fluid-state-only $^1$H image in conjunction with the two solid-state $^{31}$P and $^1$H images is shown in FIG. 7. A second RF excitation pulse for $^1$H 38 yields a fluid-state $^1$H spin echo signal 40, from which a fluid-state image of $^1$H spatial distribution can be generated. Alternatively, as shown in FIG. 8, an inversion gradient vector pulse 42 is generated to yield a gradient echo signal 44 which can be acquired for the fluid-state $^1$H.

Using either technique, this resultant fluid-state $^1$H image is subtracted from the total $^1$H image, leaving an image of just the solid-state protons. Since the proton concentration in bone mineral is considerably smaller than the proton concentration in the matrix, this resultant image in effect reflects only the matrix concentration. The matrix concentration can be quantified using techniques similar to those described above for quantifying the mineral concentration from the $^{31}$P image. The mineral-to-matrix ratio can then be calculated by dividing the mineral concentration by the matrix concentration. An image of the degree of mineralization can likewise be obtained by computing the pixel-by-pixel ratio of the images. This is a specific example of the general feature of the foregoing technique that data from one image can be processed and/or combined with data from another image to produce a new image or other data set.

Materials other than bone that can be imaged using the foregoing techniques include, without limitation, cartilage, tendon, wood and its derivatives, other agricultural materials, fibers, foodstuffs, coal, minerals, fossils, rock and other geophysical or petrochemical substances and residues, chemicals, polymers, rubbers, ceramics, glasses, gemstones, gases, fluids, gels, liquid crystalline materials, nuclear materials, and composite materials, all singly or in combination. In addition, the foregoing techniques are not limited to imaging solid-state materials, and can also be employed to image fluids, particularly fluids that exhibit broad spectral linewidth, and/or fluids in which diffusion effects severely attenuate spin or gradient echo signals.

As in the foregoing bone imaging examples, multiple images of the same specimens, using the same or different nuclear spin species, with or without variations of pulse sequence parameters, may be obtained, with or without calibration procedures, and mathematically combined or processed using the appropriate computations to produce images in which the pixel intensity values represent or reflect a property of interest.

Other embodiments are within the following claims.

What is claimed is:

1. A method for acquiring data by magnetic resonance, the method comprising:
    subjecting an object comprising a first isotope to a main magnetic field;
    subjecting the object to a pulse sequence comprising:
        a first magnetic field gradient pulse having a start and an end;
        a RF excitation pulse for exciting the first isotope, the RF excitation pulse being generated between the start and the end of the first magnetic field gradient pulse;
    acquiring RF signals emitted by the excited first isotope after the RF excitation pulse and before the end of the first magnetic field gradient pulse;
    processing the RF signals to generate data representative of a spatial distribution of the first isotope within the object.

2. The method of claim 1, wherein the step of acquiring RF signals emitted by the excited first isotope begins substantially immediately following the conclusion of the RF excitation pulse.

3. The method of claim 2, wherein the step of acquiring RF signals emitted by the excited first isotope begins less than 40 µs after the conclusion of the RF excitation pulse.

4. The method of claim 3, wherein the step of acquiring RF signals emitted by the excited first isotope begins less than 5 µs after the conclusion of the RF excitation pulse.

5. The method of claim 1, wherein the pulse sequence further comprises a second magnetic field gradient pulse, and wherein the RF excitation pulse is generated during the second magnetic field gradient pulse.

6. The method of claim 5, wherein the pulse sequence further comprises a third magnetic field gradient pulse, wherein the RF excitation pulse is generated during the third magnetic field gradient pulse, and wherein the first, second, and third magnetic field gradient pulses define a gradient vector.

7. The method of claim 6, wherein the pulse sequence is repeated a plurality of times, each pulse sequence having an associated gradient vector.

8. The method of claim 7, wherein the magnitude of the gradient vector is substantially the same in each of the plurality of times.

9. The method of claim 8, wherein the magnitude of the gradient vector is substantially between about 2 G/cm and about 12 G/cm.

10. The method of claim 9, wherein the magnitude of the gradient vector is substantially between about 2 G/cm and about 4 G/cm.

11. The method of claim 10, wherein the magnitude of the gradient vector is approximately 2 G/cm.

12. The method of claim 7, wherein the gradient vector has a different direction in at least two of the plurality of times.

13. The method of claim 12, wherein the gradient vector has a different direction in about of one thousand of the plurality of times.

14. The method of claim 7, wherein the gradient vector has a same direction in at least two of the plurality of times.

15. The method of claim 14, wherein the gradient vector has the same direction in about of four of the plurality of times.

16. The method of claim 7, wherein an interpulse repetition time TR is less than about 1.0 s.

17. The method of claim 16, wherein an interpulse repetition time TR is less than about 0.5 s.

18. The method of claim 17, wherein an interpulse repetition time TR is less than about 0.3 s.

19. The method of claim 1, wherein a rise time of the first magnetic field gradient pulse is about of 0.1 s.

20. The method of claim 1, wherein the RF excitation pulse is initiated about 200 $\mu$s after a rise time of the first magnetic field gradient pulse.

21. The method of claim 1, wherein the flip angle of the RF excitation pulse is less than about 30°.

22. The method of claim 21, wherein the flip angle of the RF excitation pulse is less than about 20°.

23. The method of claim 1, wherein the step of processing the RF signals includes Fourier transformation.

24. The method of claim 1, wherein data representative of the RF signals reside on radial lines in a spherical polar coordinate system in the k-space, wherein the points in the spherical polar coordinate system can be represented by vectors k from the origin.

25. The method of claim 1, wherein the first isotope is $^{31}$P.

26. The method of claim 25, wherein the step of processing the RF signals includes generating data representative of the density of $^{31}$P in the object.

27. The method of claim 25, wherein the object is bone.

28. The method of claim 27, further comprising the step of subjecting a calibration phantom comprising $^{31}$P to the main magnetic field and the pulse sequence.

29. The method of claim 28, wherein the step of processing the RF signals includes the step of generating an image representing the spatial density of $^{31}$P in the object and calibration phantom.

30. The method of claim 28, wherein the step of generating data representative of the density of $^{31}$P in the object includes calculating the image intensity of the object relative to the image intensity of the calibration phantom.

31. The method of claim 1, wherein the first isotope is $^{1}$H.

32. The method of claim 31, wherein the step of processing the RF signals includes generating data representative of the density of $^{1}$H in the object.

33. The method of claim 1, wherein the object further comprises a second isotope, and wherein a second RF excitation pulse excites the second isotope, and wherein RF signals emitted by the excited second isotope are acquired after the second RF excitation pulse.

34. The method of claim 33, wherein the step of processing the RF signals includes generating data representative of the spatial distribution of the second isotope within the object.

35. The method of claim 34, wherein the object is bone.

36. The method of claim 35, wherein the first isotope is $^{31}$P, and wherein the second isotope is $^{1}$H.

37. The method of claim 36, wherein the step of processing the RF signals includes generating data representative of the density of $^{31}$P in the object.

38. The method of claim 37, wherein the step of processing the RF signals includes generating data representative of the density of $^{1}$H in the object.

39. The method of claim 38, further comprising the step of acquiring RF signals emitted by the excited $^{1}$H isotope after the end of the first magnetic field gradient pulse, and wherein the step of processing the RF signals includes generating data representative of the density of fluid-state and solid-state $^{1}$H in the object.

40. The method of claim 39, wherein the step of processing the RF signals includes generating data representative of the density of substantially only fluid-state $^{1}$H in the object.

41. The method of claim 40, wherein the step of processing the RF signals includes determining a density ratio of $^{31}$P to $^{1}$H in the object.

42. The method of claim 41, wherein the step of determining the density ratio of $^{31}$P to $^{1}$H in the object comprises processing the data representative of the density of fluid-state and solid-state $^{1}$H in the object and the data representative of the density of substantially only fluid-state $^{1}$H in the object to generate data representative of the density of substantially only solid-state $^{1}$H in the object.

43. The method of claim 42, wherein the step of determining the density ratio of $^{31}$P to $^{1}$H in the object comprises dividing the data representative of the density of $^{31}$P in the object by the data representative of the density of substantially only solid-state $^{1}$H in the object.

44. Apparatus for acquiring data by magnetic resonance, the apparatus comprising:
means for subjecting an object comprising a first isotope to a main magnetic field;
means for subjecting the object to a pulse sequence comprising:
a first magnetic field gradient pulse having a start and an end;
a RF excitation pulse for exciting the first isotope, the RF excitation pulse being generated between the start and the end of the first magnetic field gradient pulse;
means for acquiring RF signals emitted by the excited first isotope after the RF excitation pulse and before the end of the first magnetic field gradient pulse;
means for processing the RF signals to generate data representative of a spatial distribution of the first isotope within the object.

45. A method for acquiring data by magnetic resonance, the method comprising:
subjecting an object comprising a first isotope to a main magnetic field;
subjecting the object to a pulse sequence comprising:
a first magnetic field gradient pulse;
a RF excitation pulse for exciting the first isotope;
acquiring RF signals emitted by the excited first isotope after the RF excitation pulse, the acquisition of RF signals beginning substantially immediately following the conclusion of the RF excitation pulse;
processing the RF signals to generate data representative of a spatial distribution of the first isotope within the object.

46. The method of claim 45, wherein the step of acquiring RF signals emitted by the excited first isotope begins less than 20 $\mu$s after the conclusion of the RF excitation pulse.

47. The method of claim 46, wherein the step of acquiring RF signals emitted by the excited first isotope begins less than 5 $\mu$s after the conclusion of the RF excitation pulse.

48. The method of claim 45, wherein the RF signals emitted by the excited first isotope are acquired during the first magnetic field gradient pulse.

49. The method of claim 45, wherein the pulse sequence further comprises a second magnetic field gradient pulse, and wherein the RF excitation pulse is generated during the second magnetic field gradient pulse.

50. The method of claim 49, wherein the pulse sequence further comprises a third magnetic field gradient pulse, and wherein the RF excitation pulse is generated during the third magnetic field gradient pulse.

51. The method of claim 45, wherein the pulse sequence is repeated a plurality of times.

52. A method for generating a magnetic resonance image of in vivo solid-state tissue, the method comprising:
positioning the tissue in a substantially static magnetic field;

subjecting the tissue to magnetic gradient pulses in at least two dimensions;

exciting first isotopes in the solid-state tissue while the tissue is subjected to the magnetic gradient pulses;

acquiring RF signals emitted by excited first isotopes after the first isotopes have been excited, and while the tissue is subjected to the magnetic gradient pulses;

processing the RF signals to generate data representative of a distribution of the first isotope within the solid-state tissue.

53. The method of claim 52, wherein the tissue is subjected to magnetic gradients in three dimensions.

54. The method of claim 53, wherein RF signals for generating a three-dimensional image of the distribution of the first isotope within the solid-state tissue are acquired in less than about 35 min.

55. The method of claim 54, wherein RF signals for generating a three-dimensional image of the distribution of the first isotope within the solid-state tissue are acquired in less than about 25 min.

56. The method of claim 52, wherein the solid-state tissue is bone.

57. The method of claim 56, wherein the data are representative of bone mineral density.

58. A method for determining the mineral density of bone, the method comprising:

positioning the bone in a substantially static magnetic field;

subjecting the bone to magnetic gradient pulses in at least two dimensions;

exciting a first isotope in the bone while the bone is subjected to the magnetic gradient pulses;

acquiring RF signals emitted by an excited first isotope after the first isotope has been excited, and while the bone is subjected to the magnetic gradient pulses;

processing the RF signals to generate data representative of a spatial distribution of the first isotope within the bone, processing the data to determine the mineral density of the bone.

59. The method of claim 58, wherein the first isotope is $^{31}P$.

60. The method of claim 58, wherein the step of processing the data includes evaluating the intensity of the data.

61. The method of claim 58, further including the step of subjecting a phantom to magnetic gradients along with the bone, and wherein the data generated during the step of processing the RF signals are also representative of the spatial distribution of the first isotope within the phantom.

62. The method of claim 61, wherein the step of processing the data includes evaluating the intensity of the data representative of the bone relative to the intensity of the data representative of the phantom.

63. The method of claim 61, wherein the phantom includes the first isotope in a first density.

64. The method of claim 63, wherein the phantom further includes the first isotope in a second density different from the first density.

65. A method for generating a magnetic resonance image of an object comprising a first compound and a second compound, the method comprising:

positioning the object in a substantially static magnetic field, a first isotope in the first compound having a first spin-lattice relaxation time $T_1$ in the static magnetic field, and a second isotope in the second compound having a second spin-lattice relaxation time $T_1$ greater than the first spin-lattice relaxation time $T_1$ in the static magnetic field;

subjecting the object to an RF excitation pulse sequence for exciting the first isotope in the first compound and the second isotope in the second compound;

acquiring a set of RF signals emitted by the excited first isotope and the excited second isotope;

obtaining from the set of acquired RF signals a first set of data representative of a distribution of substantially only the first compound within the object.

66. The method of claim 65, further comprising the step of obtaining a second set of data representative of a distribution of substantially only the second compound within the object.

67. The method of claim 65 wherein the first isotope is the same as the second isotope.

68. The method of claim 65, wherein the RF excitation pulse sequence comprises a first series of RF excitation pulses and a second series of RF excitation pulses.

69. The method of claim 68, wherein a flip angle of the first series of RF excitation pulses is different than a flip angle of the second series of RF excitation pulses.

70. The method of claim 69, wherein the step of obtaining the first set of data comprises processing the set of acquired RF signals in accordance with the flip angles of the first and second series of RF excitation pulses.

71. The method of claim 70, wherein the step of obtaining the first set of data comprises processing the set of acquired RF signals in accordance with the first and second spin-lattice relaxation times.

72. The method of claim 71, wherein the step of obtaining the first set of data comprises computing linear combinations.

73. The method of claim 72, wherein the step of obtaining the first set of data comprises subtraction.

74. The method of claim 68, wherein an interpulse repetition time of the first series of RF excitation pulses is different than an interpulse repetition time of the second series of RF excitation pulses.

75. The method of claim 74, wherein the step of obtaining the first set of data comprises processing the set of acquired RF signals in accordance with the interpulse repetition times of the first and second series of RF excitation pulses.

* * * * *

UNITED STATES PATENT AND TRADEMARK OFFICE
CERTIFICATE OF CORRECTION

PATENT NO. : 6,185,444 B1  
DATED : February 6, 2001  
INVENTOR(S) : Jerome L. Ackerman et al.

Page 1 of 1

It is certified that error appears in the above-identified patent and that said Letters Patent is hereby corrected as shown below:

<u>Title page,</u>
Item [73] Assignee: should read as follows: -- [73] Assignee: SkelScan, Inc., Boston, MA --.

Signed and Sealed this

Twenty-fifth Day of December, 2001

Attest:

JAMES E. ROGAN
*Attesting Officer*   *Director of the United States Patent and Trademark Office*

UNITED STATES PATENT AND TRADEMARK OFFICE
CERTIFICATE OF CORRECTION

PATENT NO. : 6,185,444 B1
DATED : February 6, 2001
INVENTOR(S) : Jerome L. Ackerman, Melvin J. Glimcher, and Yaotang Wu It is certified that error appears in the above-identified patent and that said Letters Patent is hereby corrected as shown below:

<u>Title page,</u>
Item [56], References Cited, OTHER PUBLICATIONS, the "Meunier et al." reference, "Nov. 1994" should be -- Nov. 1997 --.

Item [56], References Cited, OTHER PUBLICATIONS, the "Moore et al." reference, "Engl." should be -- Eng. --.

Item [56], References Cited, OTHER PUBLICATIONS, the "Ebifegha et al." reference should be deleted.

<u>Column 16,</u>
Lines 57 and 62, after "about", delete "of".

<u>Column 17,</u>
Line 4, after "about", delete "of".
Line 22, "claim 25" should be -- claim 26 --.

Signed and Sealed this

Twenty-fifth Day of June, 2002

*Attest:*

JAMES E. ROGAN
*Attesting Officer*  *Director of the United States Patent and Trademark Office*

UNITED STATES PATENT AND TRADEMARK OFFICE
CERTIFICATE OF CORRECTION

PATENT NO. : 6,185,444 B1  
APPLICATION NO. : 09/041981  
DATED : February 6, 2001  
INVENTOR(S) : Jerome L. Ackerman et al.

It is certified that error appears in the above-identified patent and that said Letters Patent is hereby corrected as shown below:

Col. 1, lines 3-4 should read,

GOVERNMENT SUPPORT
This invention was funded in part by the National Institutes of Health grant AR42258 from the National Institute of Arthritis and Musculoskeletal and Skin Diseases. The United States Government accordingly has certain rights in the invention.

Signed and Sealed this
Twenty-first Day of February, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 6,185,444 B1 | Page 1 of 1 |
| APPLICATION NO. | : 09/041981 | |
| DATED | : February 6, 2001 | |
| INVENTOR(S) | : Jerome L. Ackerman et al. | |

It is certified that error appears in the above-identified patent and that said Letters Patent is hereby corrected as shown below:

Col. 1, lines 3-4 should read,

<u>GOVERNMENT SUPPORT</u>
<u>This invention was made with government support under grant AR42258 awarded by the</u>
<u>National Institute of Health. The government has certain rights in the invention.</u>

This certificate supersedes the Certificate of Correction issued February 21, 2012.

Signed and Sealed this
Seventeenth Day of April, 2012

David J. Kappos
*Director of the United States Patent and Trademark Office*